US011689849B2

(12) United States Patent
Ferguson et al.

(10) Patent No.: US 11,689,849 B2
(45) Date of Patent: Jun. 27, 2023

(54) METHOD, APPARATUS AND COMPUTER-READABLE MEDIA TO MANAGE SEMI-CONSTANT (PERSISTENT) SOUND SOURCES IN MICROPHONE PICKUP/FOCUS ZONES

(71) Applicant: Nureva, Inc., Calgary (CA)

(72) Inventors: Richard Dale Ferguson, Okotoks (CA); Linshan Li, Calgary (CA); Mahdi Javer, Calgary (CA); Nicholas Alexander Norrie, Calgary (CA)

(73) Assignee: NUREVA, INC.

( * ) Notice: Subject to any disclaimer, the term of this patent is extended or adjusted under 35 U.S.C. 154(b) by 1003 days.

(21) Appl. No.: 16/421,908

(22) Filed: May 24, 2019

(65) Prior Publication Data
US 2019/0364359 A1 Nov. 28, 2019

Related U.S. Application Data

(60) Provisional application No. 62/675,995, filed on May 24, 2018.

(51) Int. Cl.
*H04R 3/00* (2006.01)
*H04R 3/04* (2006.01)
(Continued)

(52) U.S. Cl.
CPC ............ *H04R 3/005* (2013.01); *G10L 21/028* (2013.01); *G10L 21/0232* (2013.01); *H04R 3/04* (2013.01); *H04R 5/04* (2013.01); *G10L 2021/02166* (2013.01)

(58) Field of Classification Search
CPC .. H04R 3/005; H04R 3/04; H04R 5/04; G10L 21/0232; G10L 21/028; G10L 2021/02166
See application file for complete search history.

(56) References Cited

U.S. PATENT DOCUMENTS 5,699,437 A * 12/1997 Finn ................. G10K 11/17875
381/71.7
10,063,987 B2 8/2018 McGibney
(Continued)

OTHER PUBLICATIONS

International Search Report and Written Opinion dated Oct. 3, 2019, from PCT/CA2019/050708, 9 sheets.
(Continued)

*Primary Examiner* — Daniel R Sellers
(74) *Attorney, Agent, or Firm* — Katten Muchin Rosenman LLP

(57) ABSTRACT

Method, apparatus, and computer-readable media to manage undesired sound sources in microphone pickup/focus zones preferably mitigates one or more of the undesired sound source(s) in a space having a plurality of microphones and at least one desired sound source. Preferably, at least one microphone input receives plural microphone input signals from the plurality of microphones in the space. Preferably, the least one processor is coupled to the at least one microphone input and receives the plural microphone input signals. Preferably, the at least one processor determines plural micro-zones in the space. Preferably, the at least one processor determines a threshold sound field level for each micro-zone based on received plural microphone input signals that correspond to the one or more undesired sound source(s). Preferably, the at least one processor recognizes a desired sound source when received plural microphone input signals exceed one or more threshold sound field level.

24 Claims, 18 Drawing Sheets

(51) Int. Cl.
*G10L 21/0232* (2013.01)
*G10L 21/028* (2013.01)
*H04R 5/04* (2006.01)
*G10L 21/0216* (2013.01)

(56) References Cited

U.S. PATENT DOCUMENTS

| | | | | |
|---|---|---|---|---|
| 2013/0142342 A1* | 6/2013 | Del Galdo | ............ | H04R 3/005 381/56 |
| 2013/0258813 A1* | 10/2013 | Herre | ............... | H04R 3/005 367/135 |
| 2014/0098964 A1* | 4/2014 | Rosea | ................ | H04R 1/406 381/56 |
| 2017/0347217 A1* | 11/2017 | McGibney | ............ | H04S 7/303 |
| 2017/0366896 A1* | 12/2017 | Adsumilli | ............. | H04R 3/005 |
| 2018/0074782 A1 | 3/2018 | McGibney et al. | | |

OTHER PUBLICATIONS

Emanuël A. P. Habets and Jacob Benesty, "A Two-Stage Beamforming Approach for Noise Reduction and Dereverberation", IEEE Transactions on Audio, Speeach, and Language Processing, vol. 21, No. 5, May 2013, pp. 945-958.

Gerhard Doblinger, "An Adaptive Microphone Array for Optimum Beamforming and Noise Reduction", 14th European Signal Processing Conference (EUSIPCO 2006), Florence, Italy, Sep. 4-8, 2006, 5 sheets.

Taylor B. Spalt, Christopher R. Fuller, Thomas F. Brooks, William M. Humphreys, Jr., "A Background Noise Reduction Technique using Adaptive Noise Cancellation for Microphone Arrays", p. 1-16, available at: https://ntrs.nasa.gov/search.jsp?R=20110012472 2018-05-16T17:29:07+00:00Z.

The extended European search report completed Feb. 2, 2022, from European Application No. 19808293.5, 8 sheets.

* cited by examiner

Shows the circular coverage pattern

Side View - Microphone to micro-zone/bubble relationship perspective drawing with the axis of the microphone line in the middle of the circles

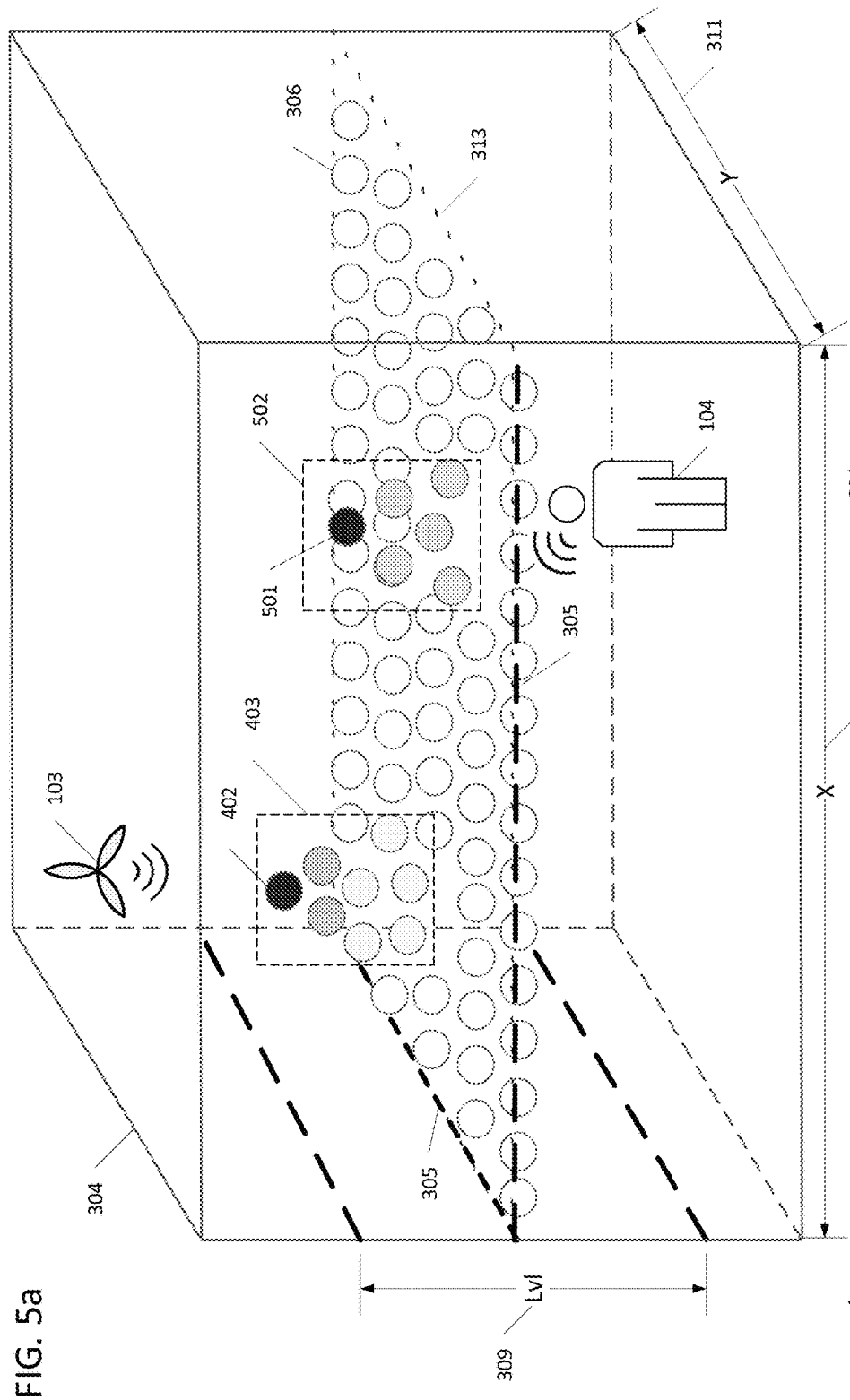
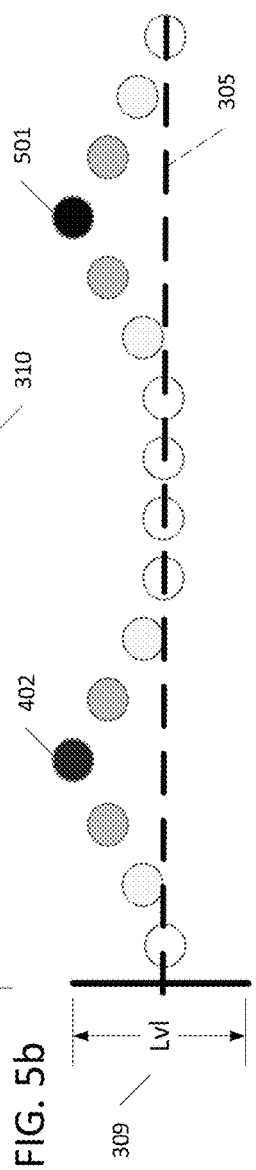
FIG. 5a
FIG. 5b

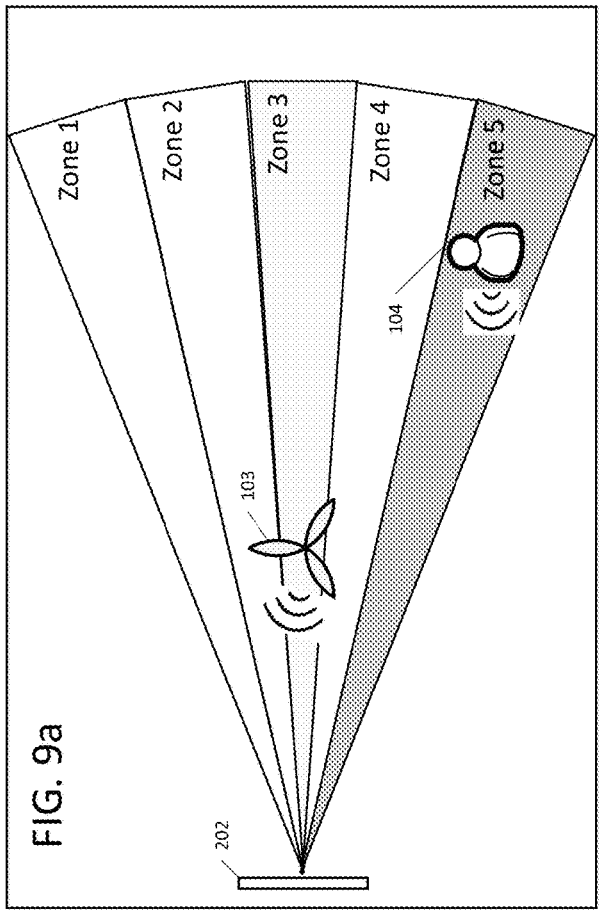
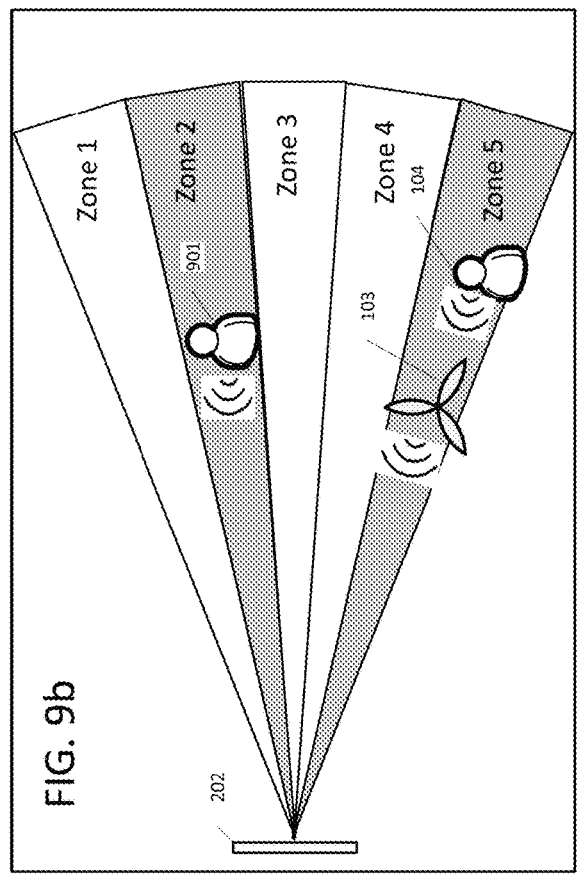

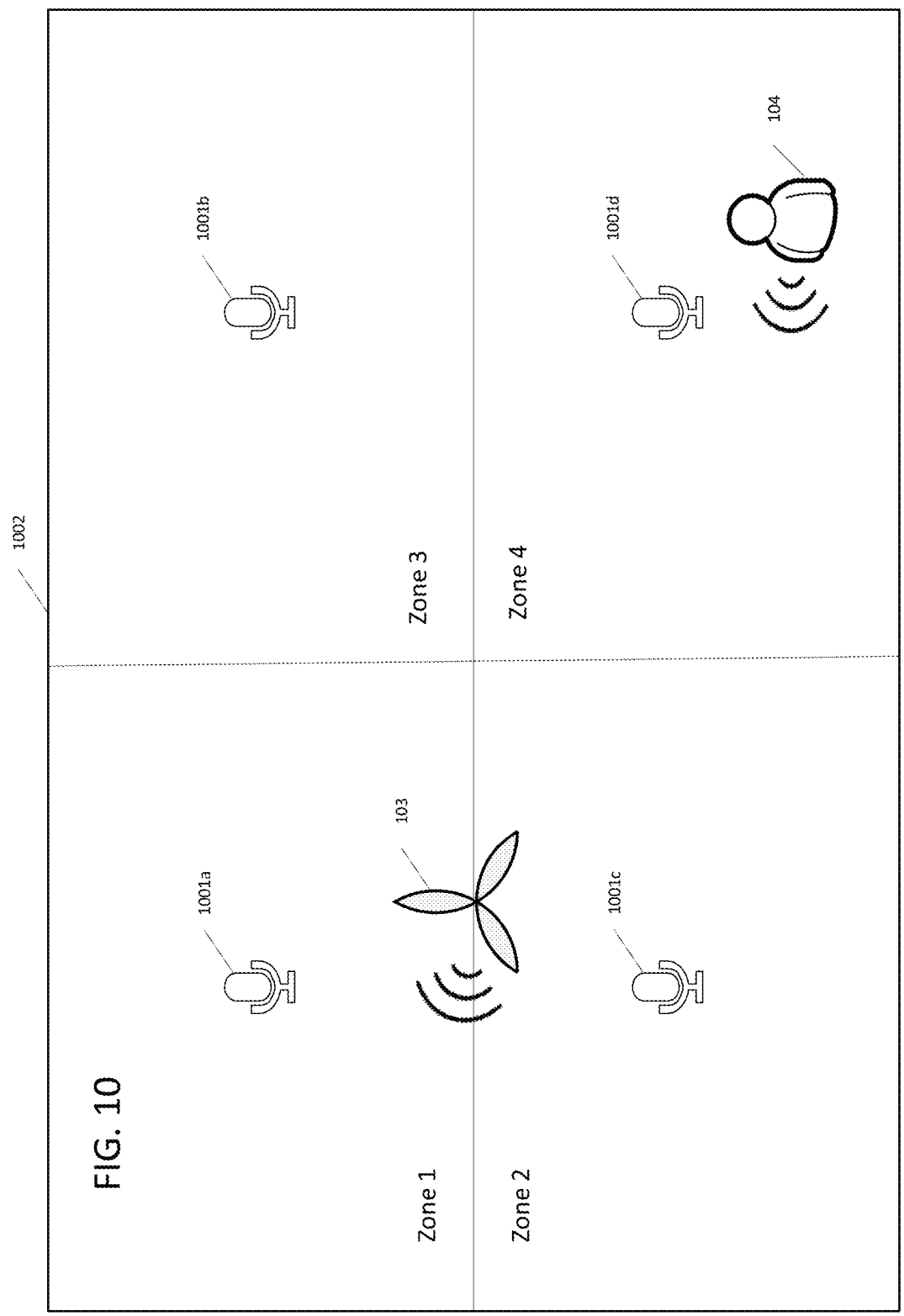

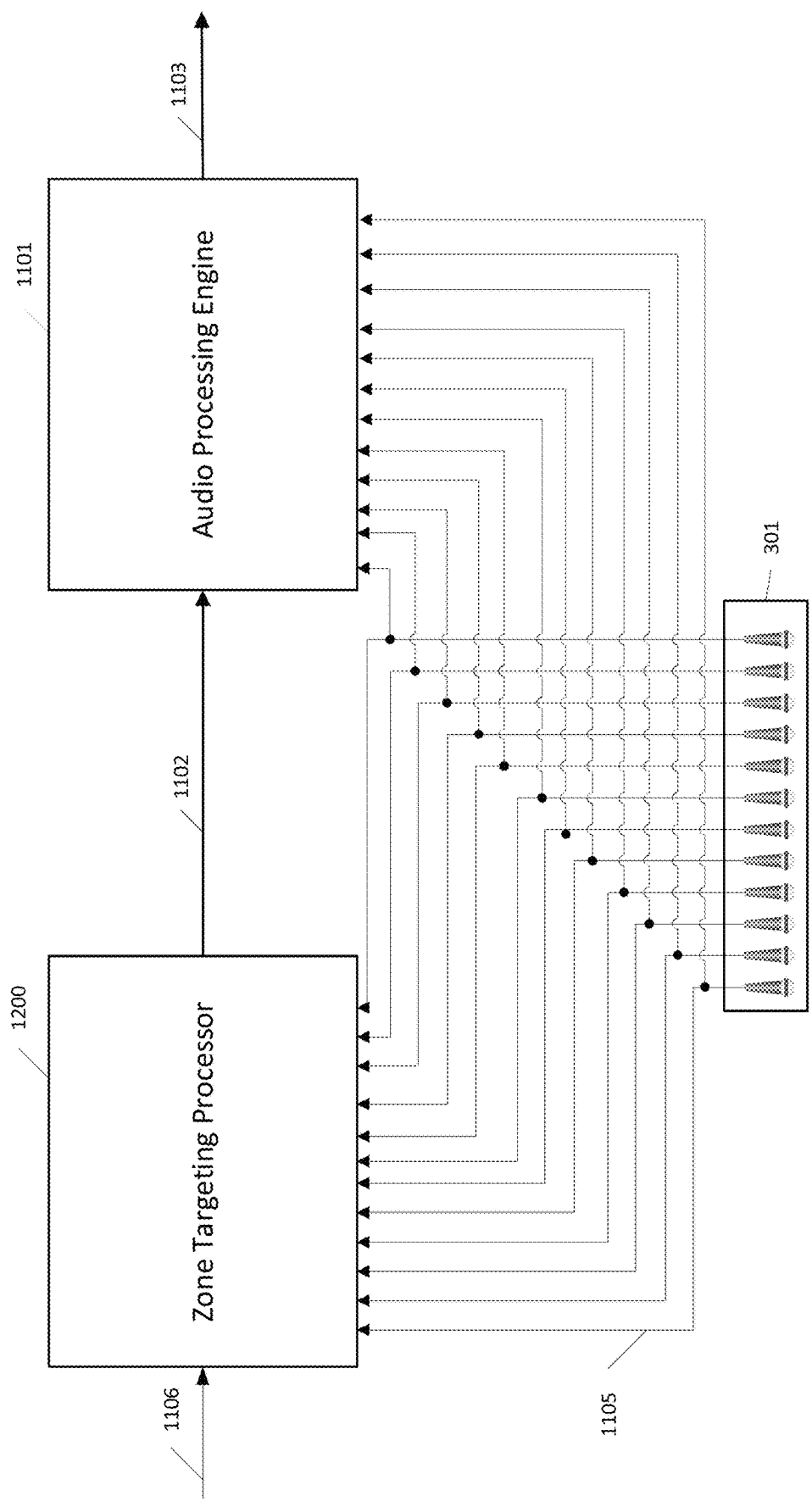
FIG. 11 High Level Architecture

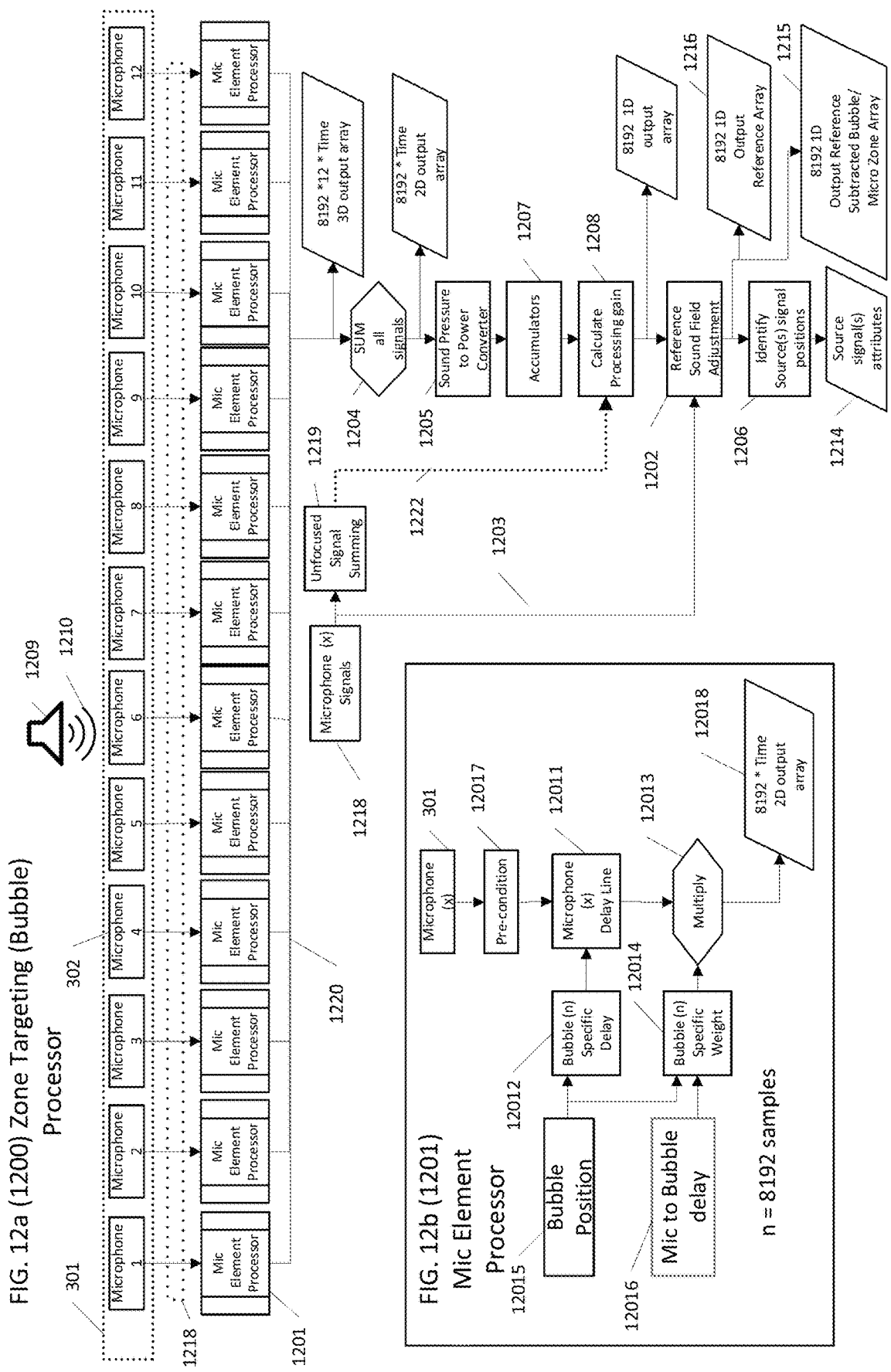

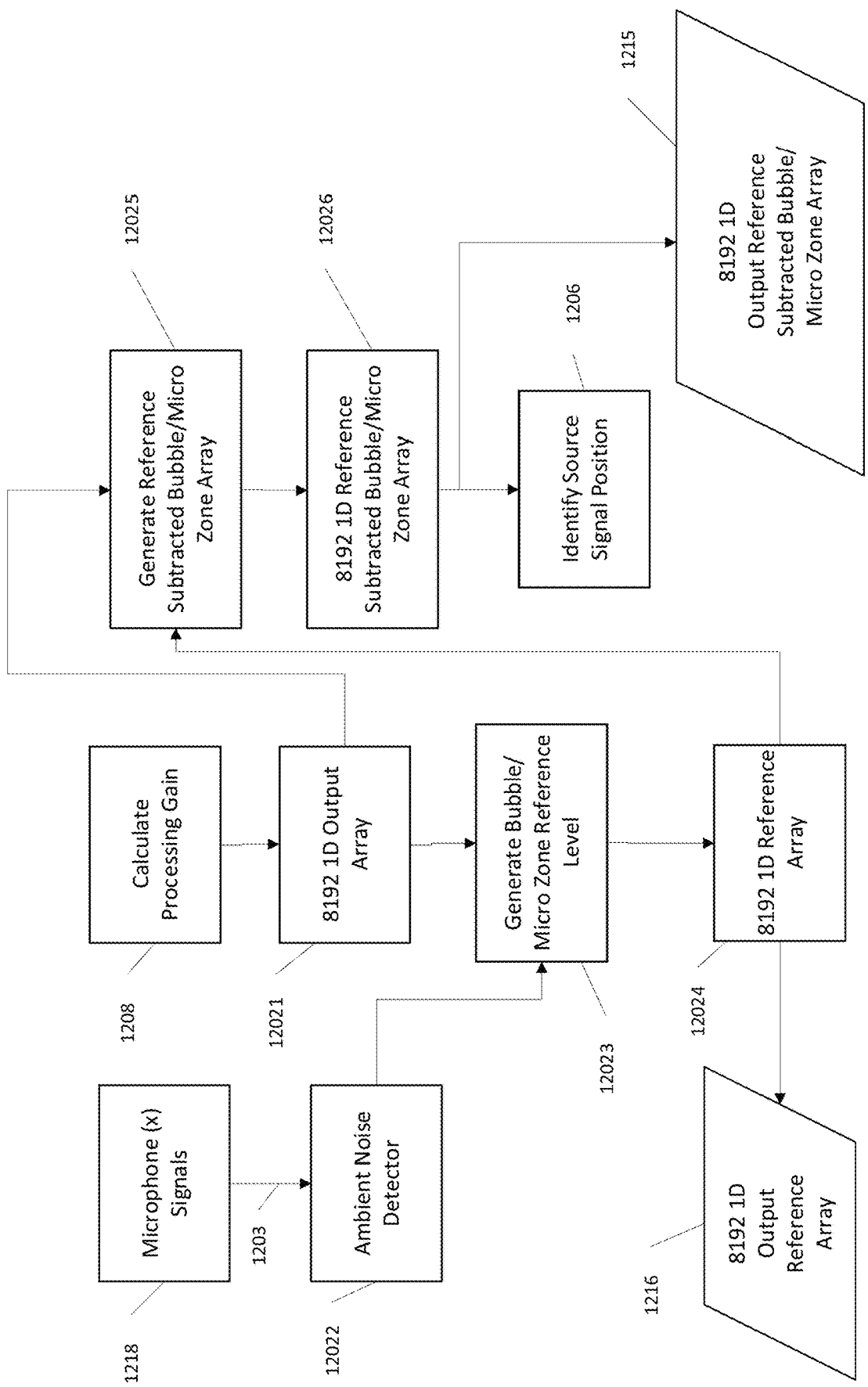

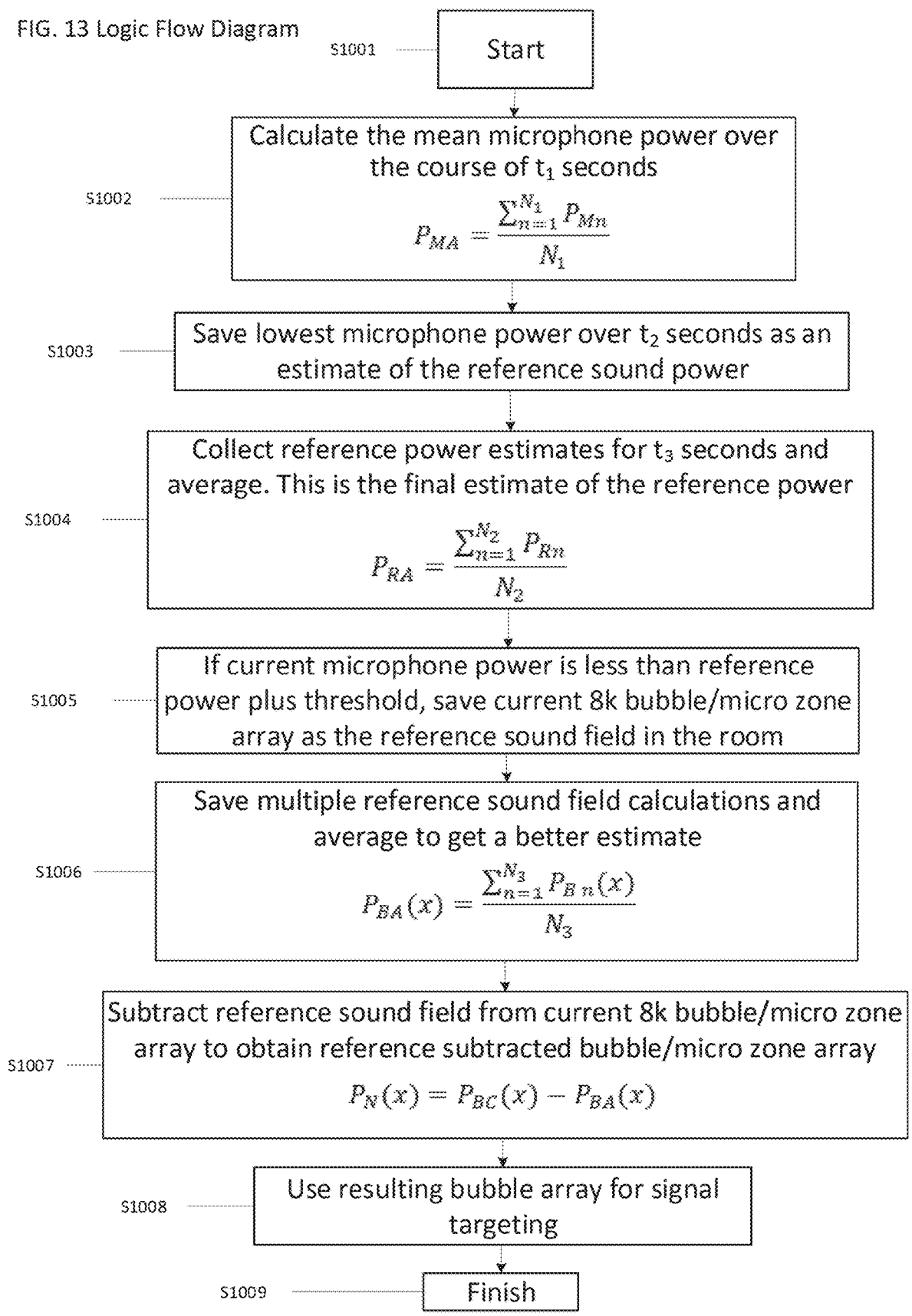
FIG. 13 Logic Flow Diagram

FIG. 14a (1400) Sound Pressure Relationships $P \sim 1/r$
P = Sound pressure
R = Distance

METHOD, APPARATUS AND COMPUTER-READABLE MEDIA TO MANAGE SEMI-CONSTANT (PERSISTENT) SOUND SOURCES IN MICROPHONE PICKUP/FOCUS ZONES

This application claims priority to U.S. Provisional Patent Appln. No. 62/675,995, filed May 24, 2018, the entire contents of which are incorporated herein by reference.

BACKGROUND OF THE INVENTION

1. Field of the Invention

The present invention generally relates to intelligently mapping a 3D spatial sound field for the purpose of dynamically identifying undesired sound source(s) within each microphone-zone and removing, excluding and/or minimizing them as potential sound source acquisition targets by establishing an individual intelligent threshold sound field level for each microphone-zone in at least near real-time to optimize desired audio signal pickup in any 3D space.

2. Description of Related Art

Locating and maintaining reliable desired sound source pickup in non-deterministic (dynamic) environments has always been difficult to manage due to, but not limited to, variable space dimensions, dynamic seating plans, roaming sound sources, unknown number(s) of microphones and locations, unknown steady state and dynamic noise, variable desired sound source levels, variable undesired sound source levels, and unknown reverberation characteristics. Typically, microphone systems need to be specifically selected, designed, and setup for each situation to manage optimum sound pickup within the dynamic environments to optimize desired sound source pick up while attempting to minimize unwanted sound source pick-up.

Traditional methods typically approach the problem with distributed microphones to enhance sound pickup, with microphones located close to the desired sound sources, and the undesired sound sources are usually more distant, but not always. This allows for good sound pick up; however, each sound source should have a microphone for best results, which increases the complexity of the hardware and installation. Usually, the system employs microphone switching and post-processing, which can degrade the audio signal through the addition of unwanted artifacts, resulting from the process of switching between microphones. If desired and undesired sound sources are equally distant to the microphone (and even less desirable where the undesired sound source is closer to the microphone), then the microphone is typically unable to distinguish between the two sound sources and will treat both as if they are the same type of sound source.

Another method to manage pick up of desired sound sources in dynamic environments is with beam forming microphone arrays which are typically located on a wall or ceiling. Most beam forming arrays are fixed-beam, but some arrays can be steered to help direct microphones to desired sound sources and theoretically optimize performance for dynamic participant locations.

In the current art, beam forming microphone arrays are configured in specific geometries to create microphone beams that can be steered towards the desired sound. The advantage of a beam array is a gain in sound quality with a relatively simple control mechanism. However, beams can only be steered in one dimension (in the case of a line array) or in two dimensions (in the case of a 2-D array). A major disadvantage of beam forming arrays is they cannot precisely locate a sound in a room; only its direction and magnitude. This means the array can locate the general direction as per a compass-like functionality, giving a direction vector based on a known sound source, which is a relative position in the environment. This method is prone to receiving equally, direct signals and potential multi-path (reverberation), resulting in false positives which can potentially steer the array to pick up undesired sound sources.

Another drawback is that the direction is a general measurement and the array cannot distinguish between desirable and undesirable sound sources in the same direction, resulting in all signals received within the beam having equal noise rejection and gain applied. If multiple sound sources are emitting, it becomes difficult to steer the array to an optimal location, especially if the sound sources are on opposite sides of the room. Undesired sound source and desired sound source levels will be different between pickup beams requiring additional post-processing which contribute artifacts and processing distortion since the post processor normalizes different beams when trying to account for variances and minimize differences to the audio streams. Since the number of microphones used tends to be limited due to costs and installation complexity, this creates issues with fewer microphones available to do sound pick-up and location determination. Another constraint with the current art is that microphone arrays do not provide even coverage of the environment due to design considerations of typical beam forming microphone arrays requiring microphones to be located in close proximity to each other. Installation of thousands of physical microphones is not typically feasible in a commercial environment due to building, shared space, hardware and processing constraints where traditional microphones are utilized, through normal methods established in the current art.

This may result in the microphone system targeting a combination of desired sound sources (persons) and undesired sound sources (semi-constant/persistent sound sources like fans, displays, etc.). Microphone systems typically are not able to differentiate desired sound sources from undesired sound sources resulting in the system targeting undesired sound sources and preventing the microphone system from passing the correct sound source signal to the audio processing engine and negatively affecting processing such as, but not limited to, automatic gain control and noise filtering parameters.

In the currently known art, there have been various approaches to manage feedback and/or unwanted sound sources; a simple microphone system will physically be switched on/off and or have a dynamic level gating function. In an on/off switched scenario, the microphone is manually turned on/off based on a decision process that takes into account the sound sources emitting at the time. In the case of the level gating function, a specific sound input level is required to turn on the microphone which will result in the microphone signal being passed through to the system. This type of system does not discriminate between desired or undesired sound sources resulting in all sound sources being passed along equally as long as a level threshold has been met. Manually switching microphones on/off is not appropriate for many situations and a microphone level gating system may miss dynamic sound source emissions depending on the situation.

In the case of an omni-directional microphone system, all sound sources are typically picked up with unity gain and will have equal effect on the audio amplifier, automatic gain control processing, and noise filtering processes. Potentially, this can significantly degrade the audio signal and prevent the system from focusing on and capturing the desired sound source. If the undesired sound source is louder than the desired sound source, the problem is even further magnified and complex post audio processing is required which may be able to address some of the audio signal problems but usually at the expense of adding other distortions to the audio signal. In the current art, to solve this problem, multiple discrete microphones can be distributed throughout the shared space, and/or adaptive or fixed directional types of microphone systems can be deployed including, but not limited to, beam-formers, directional microphones, and arrays. These solutions can work well in very specific environments; however, they have proven insufficient in overall performance and may not be able to be adequately positioned for optimum desired sound source audio pick-up while minimizing undesired sound source pick-up.

To help address this situation, typical microphone systems in the current art will track and identify the sound source with the largest amplitude, power, and/or gain signal and adjust all audio and filtering parameters accordingly. If the undesired sound source is louder than the desired sound source, the microphone system parameters will be adjusted for the undesired sound source and will be incorrect and not optimal for when and if the microphone system switches to the desired sound source.

If the undesired sound source is located closer to or between the desired sound source and the microphone system, the ability of the microphone system to target and focus on the desired sound source becomes even more problematic.

Further complex scenarios manifest when the sound space environment is uncontrolled and dynamic in nature such that the addition of incremental desired sound sources and undesired sound sources increases opportunities for the microphone system to pick up undesired sound sources, potentially creating environments outside the design criteria of the microphone system, or the system is just not able to handle properly with predetermined microphone system settings, positioning and number of microphones deployed. This situation potentially results in improper sound source pick up, improper pick up zone activation, and the potential to ignore or block desired sound sources from being detected by the microphone system.

Multiple sound sources can create a complex and difficult situation for the microphone system to locate, identify, and pick up the desired sound source(s) in the presence of undesired sound source(s), and highlighting where an intelligent audio targeting system may be required.

Thus, the current art is not able to provide adequate targeting of desired sound sources and sufficient audio performance in regard to acceptable audio pick-up and communication taking into account multiple undesired and desired sound sources in complex shared sound spaces.

Paper 1: "A Two-Stage Beamforming Approach for Noise Reduction and Dereverberation", Emanuel A. P. Habets and Jacob Benesty, IEEE TRANSACTIONS ON AUDIO, SPEECH, AND LANGUAGE PROCESSING, VOL. 21, NO. 5, MAY 2013 describes a two-stage beamforming approach presented for de-reverberation and noise reduction. In the first stage, a signal-independent beam-former is used to generate a reference signal which contains a de-reverberated version of the desired speech signal, as received at the microphones, and residual noise. In the second stage, the filtered microphone signals and the noisy reference signal are used to obtain an estimate of the de-reverberated desired speech signal. In this stage, different signal-dependent beam-formers can be used depending on the desired operating point in terms of noise reduction and speech distortion. The presented performance evaluation demonstrates the effectiveness of the proposed two-stage approach.

Paper 2: "AN ADAPTIVE MICROPHONE ARRAY FOR OPTIMUM BEAMFORMING AND NOISE REDUCTION", Gerhard Doblinger, 14th European Signal Processing Conference (EUSIPCO 2006), Florence, Italy, Sep. 4-8, 2006 presents a new adaptive microphone array efficiently implemented as a multi-channel FFT-filter bank. The array design is based on a minimum variance distortionless response (MVDR) optimization criterion. MVDR beam-former weights are updated for each signal frame using an estimated spatio-spectral correlation matrix of the environmental noise field. Matrix inversion is avoided by means of an iterative algorithm for weight vector computation. The beam-former performance is believed to be superior to designs based on an assumed homogeneous diffuse noise field. The design also is believed to outperform LMS-adaptive beam-formers at the expense of a higher computational load. Additional noise reduction is achieved with the well-known beam-former/post-filter combination of the optimum multi-channel filter. An Ephraim-Malah spectral amplitude modification with minimum statistics noise estimation is employed as a post-filter. Experimental results are presented using sound recordings in a reverberant noisy room.

Paper 3: "A Background Noise Reduction Technique using Adaptive Noise Cancellation for Microphone Arrays", Taylor B. Spalt, Christopher R. Fuller, Thomas F. Brooks, William M. Humphreys, Jr., available at: https://ntrs.nasa.gov/search.jsp?R=20110012472 2018-05-16T17:29:07+00:00Z. Background noise in wind tunnel environments poses a challenge to acoustic measurements due to possible low or negative Signal to Noise Ratios (SNRs) present in the testing environment. This paper overviews the application of time domain Adaptive Noise Cancellation (ANC) to microphone array signals with an intended application of background noise reduction in wind tunnels. An experiment was conducted to simulate background noise from a wind tunnel circuit measured by an out-of-flow microphone array in the tunnel test section. A reference microphone was used to acquire a background noise signal which interfered with the desired primary noise source signal at the array. The technique's efficacy was investigated using frequency spectra from the array microphones, array beamforming of the point source region, and subsequent deconvolution using the Deconvolution Approach for the Mapping of Acoustic Sources (DAMAS) algorithm. Comparisons were made with the conventional techniques for improving SNR of spectral and Cross-Spectral Matrix subtraction. The method was seen to recover the primary signal level in SNRs as low as −29 dB and outperform the conventional methods. A second processing approach using the center array microphone as the noise reference was investigated for more general applicability of the ANC technique. It outperformed the conventional methods at the −29 dB SNR but yielded less accurate results when coherence over the array dropped.

SUMMARY OF THE INVENTION

An object of the present embodiments is to allow for a substantially improved targeting of desired sound source(s) in the presence of dynamic and complex undesired sound sources regardless of the dynamic nature of the environment and the 3D sound field in which the microphone system is deployed. And, more specifically, it is an object of the invention to preferably establish an intelligent threshold sound field level for each microphone-zone to substantially reduce/mitigate/ignore incorrect and undesired sound source targeting by the zone target processer in the current art. The intelligent threshold sound field levels for microphone-zones may be determined in real-time, near real-time or even offline and subsequently loaded for use. That is, the present embodiments include the ability to capture background noise levels, process them offline, and then downloading the calculated thresholds to one or more devices. This ability to use the intelligent threshold sound field level on a per microphone-zone basis by the zone target processor overcomes the limitations of the prior art, which is limited to accurate and generalized sound control methods.

According to one aspect of the present invention, shared spaces and multi-use environments contain a combination of desired and undesired sound sources. These environments can be divided into any number of zones where an intelligent threshold level can be established to determine the existence of persistent or semi-persistent undesired sound sources. Using this information, undesired sound sources can be excluded from targeting in the microphone system resulting in only desired sources being selected for processing.

By eliminating the possibility that an undesired sound source can overpower a desired source, the desired sound source takes precedence over undesired sources and be detected more clearly. Also, by removing undesired sources from targeting consideration, the system is able to reduce the number of instances where switching between desired and undesired sound sources occurs, thereby improving consistency in audio pickup and noise levels; especially in systems with an Automatic Gain Control (AGC) feature.

Typical solutions in the current art attempt many methods to reduce noise from the processed microphone signals. However, these methods utilize algorithms executed late in the audio processing path and have no clear indication of which content in the audio signal is desired or undesired. Papers 1, 2 and 3 discuss many of the issues related to current art beamforming devices and methods attempted to improve audio signal quality using various post-processing techniques. These techniques typically lead to some amount of degradation of the desired signal along with variation or 'pumping' of the undesired background noise sources due to AGC processing when undesired sources are targeted by the beamforming device. In contrast, a notable aspect of the present embodiments is to eliminate targeting of undesired sound sources by these types of devices, as well as any device comprised of a plurality of microphones and sound sources (both desired and undesired). By excluding undesired sources at the front of the audio processing chain, desired signals compose the bulk of signals passed to latter stage processing algorithms, which are then better able to remove residual traces of the undesired signals without distorting or removing the desired signals.

According to a further aspect of the present invention, the spatial microphone-zone sound field is a 2D (x,y) space.

According to another aspect of the present invention, the spatial microphone-zone sound field is a 3D (x, y, and z) space.

According to yet another aspect of the present invention, the intelligent threshold sound field level comprises a derived level based on the audio characteristics defined by the undesired sound source.

The present invention provides a real-time adaptable, intelligent threshold, sound field levels-per-microphone-zone solution to minimize targeting of undesired sound sources and thus targeting desired sound sources within a plurality of sound sources and dynamic environments.

The present invention can also be embodied by capturing background noise levels in an environment; utilizing offline processing to determine the intelligent threshold sound field levels for microphone-zones; and loading the intelligent threshold sound field levels for microphone-zones into a device for use. This embodiment provides improved performance over current art devices.

The preferred embodiments comprise both algorithms and hardware accelerators (such as but not limited to Application Specific Integrated Circuits or Field Programmable Gate Arrays) to implement the structures and functions described herein.

According to a first aspect of the preferred embodiments, apparatus mitigating one or more undesired sound source(s) in a space having a plurality of microphones and at least one desired sound source, includes at least one microphone input that receives plural microphone input signals from the plurality of microphones in the space. At least one processor, coupled to the at least one microphone input, receives the plural microphone input signals. The at least one processor determines plural micro-zones in the space. The at least one processor also determines a threshold sound field level for each micro-zone based on received plural microphone input signals that correspond to the one or more undesired sound source(s) in the space. The at least one processor recognizes a desired sound source when received plural microphone input signals exceed one or more threshold sound field level.

According to a second aspect of the preferred embodiments, a method of mitigating one or more undesired sound source(s) in a space having a plurality of microphones and at least one desired sound source, includes: (i) using at least one microphone input to receive plural microphone input signals from the plurality of microphones in the space; and (ii) using at least one processor, coupled to said at least one microphone input and receiving the plural microphone input signals, to: (iia) determine plural micro-zones in the space; (iib) determine a threshold sound field level for each micro-zone based on received plural microphone input signals that correspond to the one or more undesired sound source(s) in the space; and (iic) recognize a desired sound source when received plural microphone input signals exceed one or more threshold sound field level.

According to a third aspect of the preferred embodiments, program code embodied in non-transitory computer readable media for mitigating one or more undesired sound source(s) in a space having at least one microphone and at least one desired sound source, said program comprising instructions causing at least one processor to: (i)
    use at least one microphone input to receive plural microphone input signals from the plurality of microphones in the space; (ii) use at least one processor, coupled to said at least one microphone input and receiving the plural microphone input signals, to: (iii)
    determine plural micro-zones in the space; (iv)
    determine a threshold sound field level for each micro-zone based on received plural microphone input signals that correspond to the one or more undesired sound source(s) in the space; and (v) recognize a desired sound source when received plural microphone input signals exceed one or more threshold sound field level.

BRIEF DESCRIPTION OF THE DRAWINGS

FIGS. 5a and 5b are diagrammatic illustrations of a 2D sound field map and visualization of the sound field reference level with both desired and undesired sound sources.

FIGS. 9a and 9b are diagrammatic illustrations of applying an intelligent threshold sound field level to the zones of a beam-former array typical in the current art.

FIG. 10 is a diagrammatic illustration of applying an intelligent threshold sound field level to a discrete microphone system typical in the current art.

FIG. 11 is a high-level architecture diagram of an embodiment of the present invention.

FIGS. 12a and 12b are a structural and functional diagram of the bubble processor and the microphone element processor, according to an embodiment of the present invention. FIG. 12b includes a flow chart for calculating processing gain.

FIG. 12c is a structural and functional diagram of the bubble processor's reference sound removal algorithm.

FIG. 13 is a logical diagram of the current implementation of the technology, outlining a flow according to a preferred embodiment, from start to finish.

FIGS. 14a and 14b are diagrammatic illustrations of sound pressure correlated with distance.

Figure 1:
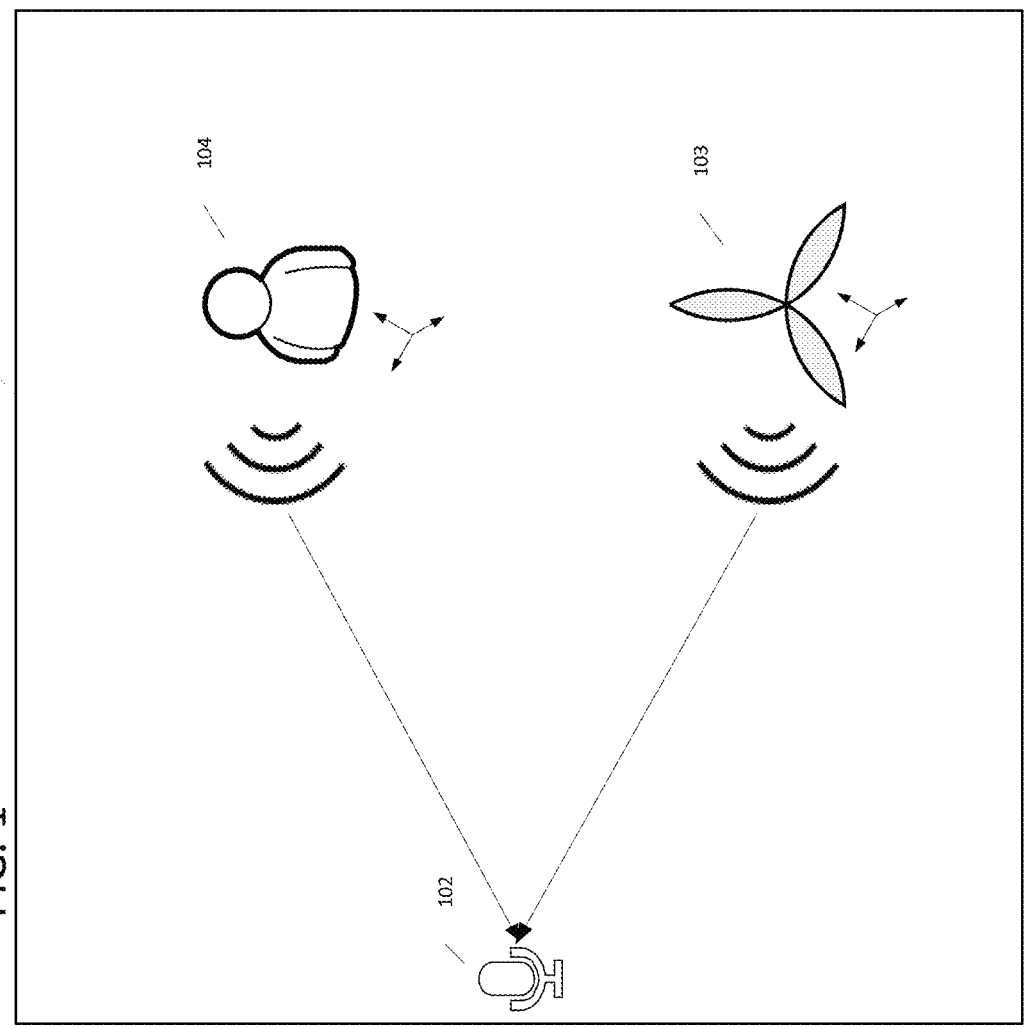
FIG. 1 is a diagrammatic illustration of undesired and desired sound sources.

DETAILED DESCRIPTION OF THE
PRESENTLY PREFERRED EXEMPLARY
EMBODIMENTS

The present invention is directed to apparatus and methods that enable sound capture and communication systems to consistently capture desired sound sources in the presence of undesired sound sources in real-time employing microphones for audio capture and communication systems, personal computers, network workstations, or other similarly connected appliances, without manual intervention, to engage in effective audio pickup in undetermined environments (spaces) with unknown number(s) of desired and undesired sound sources.

Advantageously, embodiments of the present apparatus and methods afford an ability to provide an end user experience having all desired sound sources identified and transmitted, with significantly reduced interference from undesired sound sources, regardless of the number of undesired sound sources, while maintaining optimum audio quality for all audio pickup situations.

A notable challenge to identifying and removing undesired sound sources from the targeting processor is determining the location and the amplitude of undesired sound sources relative to desired sources. When undesired sound sources are of sufficient amplitude to overwhelm desired sources, current art systems will preferentially target the undesired source resulting in (i) loss of audio pick up as the system targets only the undesired source (ii) reduced pick up and audio quality as the system continuously switches between the desired and undesired sound sources.

Another notable challenge to identifying and removing undesired sound sources from the targeting processor is each switch between targeted sources often requires a minimum amount of time to eliminate introduction of artifacts, such as a change in signal frequency (known as the Doppler Effect) into the desired signal. Each transition to an undesired sound source will also impose a change or 'pumping' in transmitted noise level as Automatic Gain Control (AGC) and noise suppression mechanisms engage to provide a consistent output amplitude.

A "desired sound source" in this specification may include, but is not limited to, one or more of, a combination of audio sources such as: sound sources that have frequency and time domain attributes, specific spectral signatures, and/or any audio sounds that have amplitude, power, phase, frequency and time, and/or voice characteristics that can be measured and/or identified such that at least one intelligent threshold criterion can be set to identify the sound source as desired.

An "undesired sound source" in this specification may include, but is not limited to, one or more of, a combination of persistent or semi-persistent audio sources such as: sound sources that may be measured to be constant over a configurable specified period of time, have a predetermined amplitude response, have configurable frequency and time domain attributes, specific spectral signatures, and/or any audio sounds that have amplitude, power, phase, frequency and time characteristics that can be measured and/or identified such that an intelligent threshold criteria can be set to identify the sound source as undesired. These undesired sources encompass, but are not limited to, Heating, Ventilation, Air Conditioning (HVAC) fans and vents; display projector fans and electronic components; computer display fans and electronic components; white noise/sound mask generators; any other types of persistent or semi-persistent electronic or mechanical sound sources.

A "microphone" in this specification may include, but is not limited to, one or more of, any combination of transducer device(s) such as, condenser mics, dynamic mics, ribbon mics, USB mics, stereo mics, mono mics, shotgun mics, boundary mic, small diaphragm mics, large diaphragm mics, multi-pattern mics, strip microphones, Micro-Electro Mechanical Systems (MEMS) mics, digital microphones, fixed microphone arrays, dynamic microphone arrays, beam forming microphone arrays, and/or any transducer device capable of receiving acoustic signals and converting them to electrical signals, and/or digital signals.

A "microphone-zone" in this specification may include, but is not limited to, one or more of, any combination of microphone pickup patterns such as, physical microphones, virtual microphones, bubbles, macro-zones, micro-zones, beams, adaptive zones, omni, cardioid, hyper-cardioid, super-cardioid, lobar, bidirectional, directional, and/or any microphone pickup area and pattern capable of receiving acoustic signals within an arbitrary or defined boundary area, and or position. For example, see U.S. patent application Ser. No. 15/597,646, filed May 17, 2017 (allowed), METHOD, APPARATUS, AND COMPUTER-READABLE MEDIA FOR FOCUSSING SOUND SIGNALS IN A SHARED 3D SPACE, now U.S. Pat. No. 10,063,987, issued Aug. 28, 2018, incorporated herein by reference.

A "device" in this specification may include, but is not limited to, one or more of, or any combination of processing device(s) such as, processor(s), a cell phone, a Personal Digital Assistant, a smart watch or other body-borne device (e.g., glasses, pendants, rings, etc.), a personal computer, a laptop, a pad, a cloud-access device, a white board, and/or any device capable of sending/receiving messages to/from a local area network or a wide area network (e.g., the Internet), such as devices embedded in cars, trucks, aircraft, household appliances (refrigerators, stoves, thermostats, lights, electrical control circuits, the Internet of Things, etc.).

An "engine" is preferably a program that performs a core function for other programs. An engine can be a central or focal program in an operating system, subsystem, application program or hardware/firmware system that coordinates the overall operation of other programs. It is also used to describe a special-purpose program containing an algorithm that can sometimes be changed. The best-known usage is the term search engine which uses an algorithm to search an index of topics given a search argument. An engine is preferably designed so that its approach to searching an index, for example, can be changed to reflect new rules for finding and prioritizing matches in the index. In artificial intelligence, for another example, the program that uses rules of logic to derive output from a knowledge base is called an inference engine.

As used herein, a "server" may comprise one or more processors, one or more Random Access Memories (RAM), one or more Read Only Memories (ROM), one or more user interfaces, such as display(s), keyboard(s), mouse/mice, etc. A server is preferably apparatus that provides functionality for other computer programs or devices, called "clients." This architecture is called the client-server model, and a single overall computation is typically distributed across multiple processes or devices. Servers can provide various functionalities, often called "services", such as sharing data or resources among multiple clients, or performing computation for a client. A single server can serve multiple clients, and a single client can use multiple servers. A client process may run on the same device or may connect over a network to a server on a different device. Typical servers are database servers, file servers, mail servers, print servers, web servers, game servers, application servers, and chat servers. The servers discussed in this specification may include one or more of the above, sharing functionality as appropriate. Client-server systems are most frequently implemented by (and often identified with) the request-response model: a client sends a request to the server, which performs some action and sends a response back to the client, typically with a result or acknowledgement. Designating a computer as "server-class hardware" implies that it is specialized for running servers on it. This often implies that it is more powerful and reliable than standard personal computers, but alternatively, large computing clusters may be composed of many relatively simple, replaceable server components.

The servers and devices in this specification typically use the one or more processors to run one or more stored "computer programs" and/or non-transitory "computer-readable media" to cause the device and/or server(s) to perform the functions recited herein. The media may include Compact Discs, DVDs, ROM, RAM, solid-state memory, or any other storage device capable of storing the one or more computer programs.

FIG. 1 is illustrative of the general emitted audio sources 103, 104 arriving at a typical microphone system 102 which has been configured in a non-specific environment 101. The microphone system 102 setup in the environment 101 will typically be configured to pick-up desired sound source(s) (e.g., persons, machinery, animals, etc.) 104 which may be emitting directly into a microphone system 102, or the desired sound source 104 may be at a non-specified distance to the microphone system 102 (may be moving). The microphone system 102 will also pick up any undesired sound source(s) (e.g., fan, HVAC, vacuums, sirens, etc.) 103 emitting sound such that it is picked up by the microphone system 102 within an environment 101. The undesired sound source(s) 103 may be close to the microphone system 102, or may be at an unspecified distance removed from the microphone system 102. It should be noted that although a singular desired sound source 104, and a singular undesired sound source 103 are illustrated, it is within the preferred disclosure to support any number of desired 104 and any number of undesired 103 sound sources that may be statically positioned, dynamically positioned, in motion, and of steady state and/or variable amplitude and duration, including fully off and fully on.

When the sound source(s) are static, with known locations, as in not moving, microphone systems 102 can be highly configured to optimize desired sound source 104 pickup and minimize undesired sound source 103 pickup. In a typical environment 101 desired sound source(s) 104 may be positioned anywhere in the environment 101 and may be mobile, and undesired sound source(s) 103 may also be dynamically moving, and may vary in position, duration, and amplitude, thus making it problematic for the microphone system 102 to adjust and perform optimally under less than ideal situations where all the sound sources and microphone positions cannot be controlled.

It should be noted that an environment 101 for the purpose of this disclosure may be, but not limited to, any space that may have a microphone pickup system deployed such as, but not limited to, conference rooms, collaboration areas, recording studios, public and private auditoriums, venues, public addresses, drive-through, motor vehicles, aircraft, ships, and/or any space where microphone(s) are deployed to pick up desired sounds 104 in the presence of undesired sound sources 103.

FIGS. 2a, 2b, 2c, 2d, 2e, 2f and 2g are illustrative examples in the current art of a more complex microphone system 202 that contains either a combination of directional microphones, microphones configured to work in a fixed or adaptive beamforming array, or any configurable microphone system that is capable of configuring and using any number of pick up zones to isolate, target, and/or steer to sound sources.

Figure 2A:
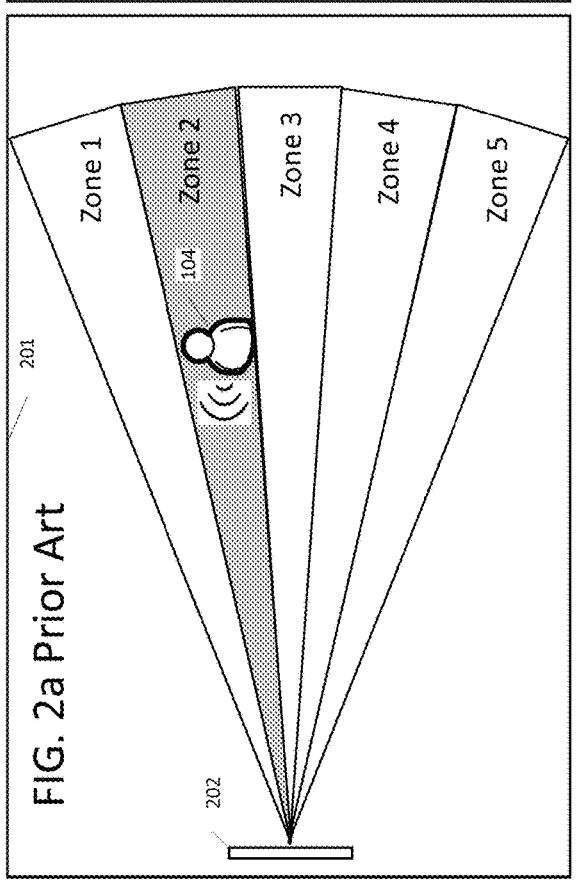
FIGS. 2a, 2b, 2c, 2d, 2e, 2f, and 2g are, respectively, prior art illustrative diagrams of microphone system limitations.
Figure 2B:
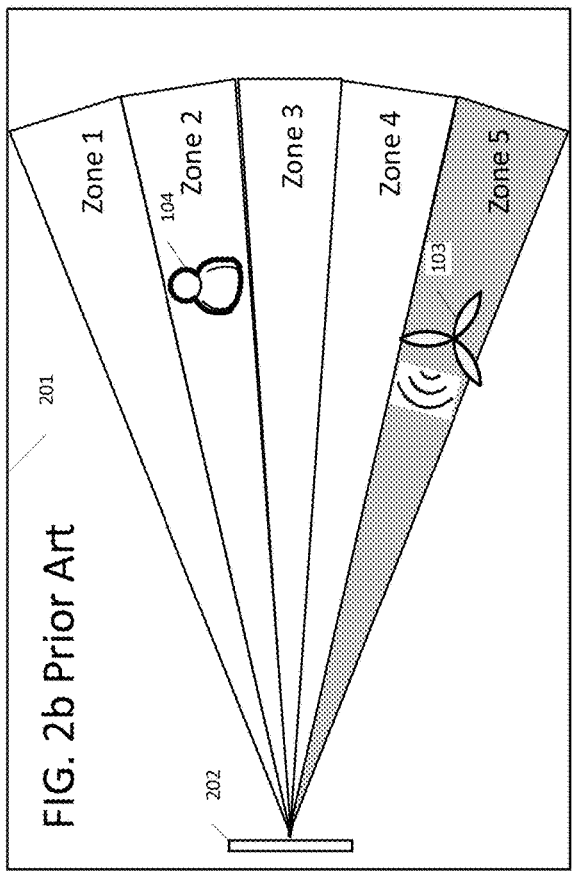

FIG. 2a illustrates a microphones system 202 installed in an environment 201. The microphone system 202 is configured to utilize 5 large pick-up zones (Zone 1, Zone 2, Zone 3, Zone 4, and Zone 5). A desired sound source 104 is located within Zone 2. The microphone system 202 tracks to the desired sound source 104 and determines that the desired sound source is within Zone 2 and, as a result, enables Zone 2 while typically minimizing the microphone pick-up in the remaining zones (Zone 1, Zone 3, Zone 4 and Zone 5). In FIG. 2b the desired sound source 104 stopped emitting sound and an undesired sound source 103 started emitting sound. The microphone system 202 identified a sound source was present and switched the microphone system 202 to target Zone 5. The undesired sound source 103 and desired sound source 104 are treated equally by the microphone system 202 causing the microphone system to target and steer to any active sound source. As a result, the microphone system reacted to an undesired sound source 103 and will pass the undesired sound source 103 through to the audio processing engine.

Figure 2C:
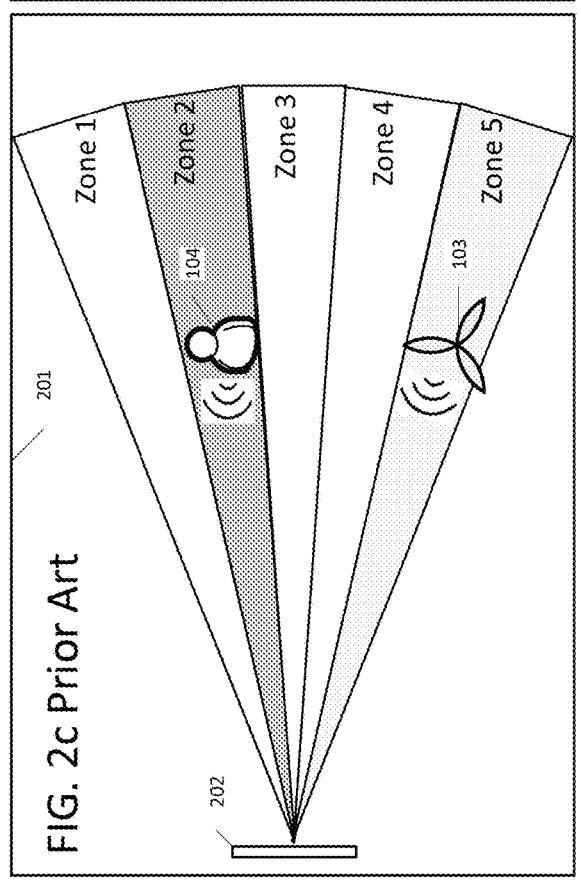
Figure 2D:
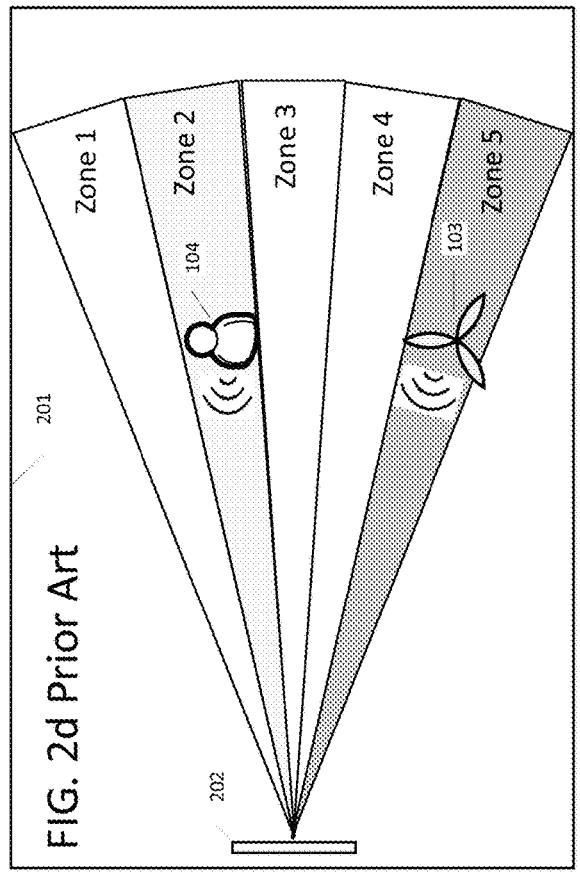

If the sound sources 103, 104 as illustrated in FIGS. 2c and 2d are emitting sound at the same time, the microphone system 202 through potentially complex logic will either target and switch to the desired sound source 104 in Zone 2 if it is louder or target and switch to the undesired sound source 103 in Zone 5 if it is louder. This can cause the microphone system 202 to switch back and forth depending on the sound source level(s) of the sources 103, 104, and can cause the microphone system 202 to adjust and compensate for the different types of sound sources 103, 104 in real time which can show up as undesired Automatic Gain Control (AGC) adjustments, irregular noise performance, and levels with complex filtering being required. As the microphone system 202 switches between Zones there is potential for loss of the desired sound source 104 signal which exacerbates the problem of obtaining optimal desired sound source 104 audio. Typically, undesired sound source(s) 103 are unpredictable in level and duration which makes it difficult to set manual configuration parameters such as signal/noise threshold levels, and switched microphone logic based on sound levels without risking loss of signal and false positive microphone system 202 targeting of undesired sound sources 103.

Figure 2F:
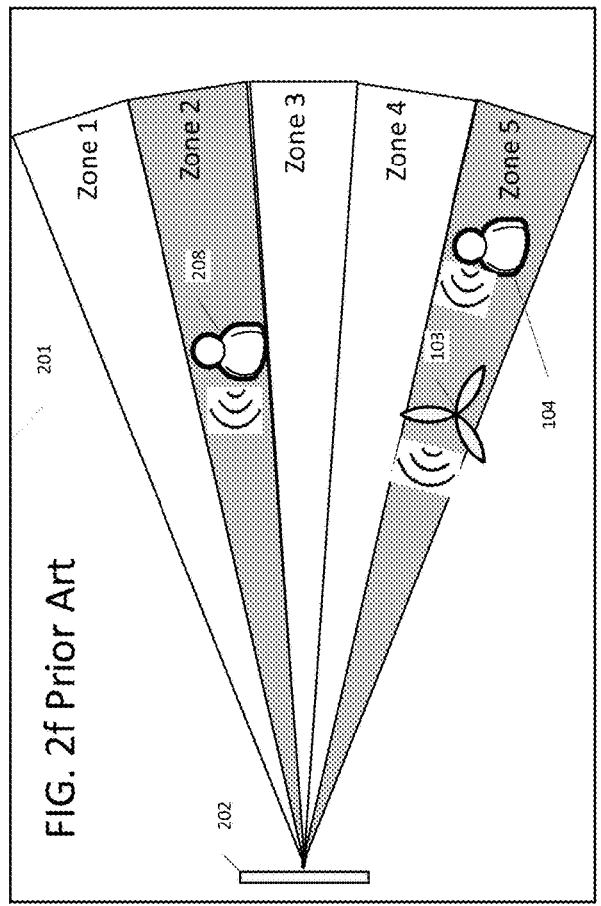
Figure 2E:
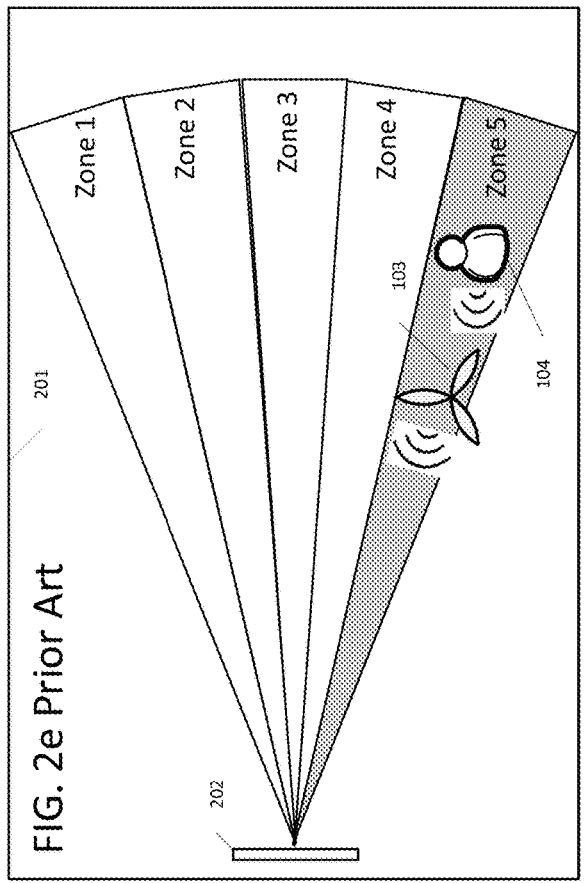

FIGS. 2e, and 2f further illustrate challenges in the current art with typical pick up zone size and location of multiple sound sources situated within a beamforming array 202 zones If the desired sound source 104 and the undesired sound source 103 are located within the same zone as shown in FIG. 2e, the microphone system 202 is unable to distinguish and preferably separate the two sound sources 104, 103, and as a result both signals get treated equally and passed through the microphone system 202 creating an audio signal containing a significant amount of undesired sound signal. In the case of FIG. 2f, the problem is further compounded by the addition of another desired sound source 208. The desired sound source 208 will need to compete with both sound sources 103,104 in Zone 5, potentially resulting in a situation that systems in the current art are not able to handle adequately.

Figure 2G:
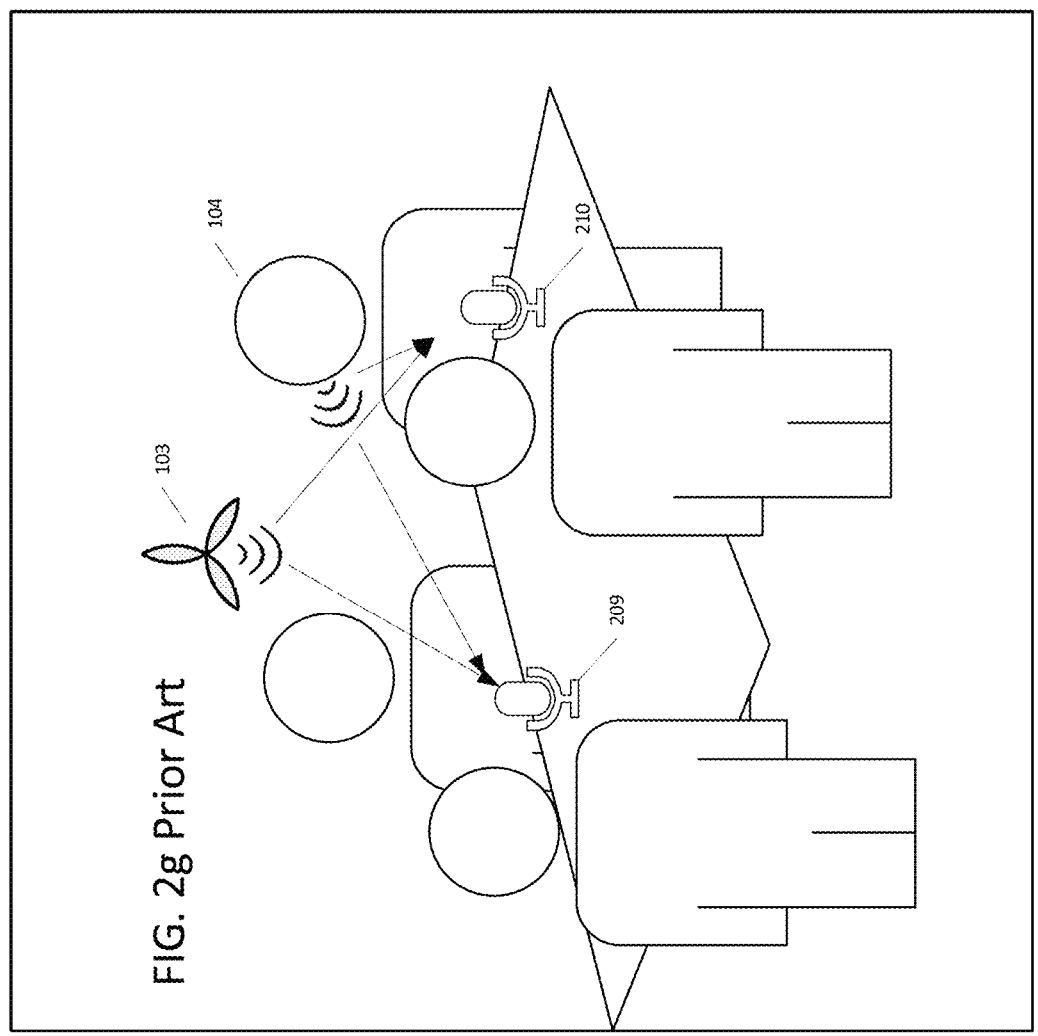

FIG. 2g illustrates a situation in which discrete microphones 209, 210 are installed in a table top conference room environment. The conference room environment contains an undesired sound source 103 and desired sound sources 104. The two discrete microphones 209, 210 as a function of their location and polar pick up patterns will create two zones that may have some overlap in pick up coverage. This creates a scenario where microphones 209, 210 may need to be turned on and off (switched) limiting the effective zone coverage or, as in FIG. 2f, both Zones are enabled, resulting in poor audio pickup as the undesired sound source 103 is equally picked up with the desired sound source 104. In both instances, audio pickup performance is not optimized to the dynamic audio situation and participant locations and speaking levels during the audio conference.

Figure 3A:
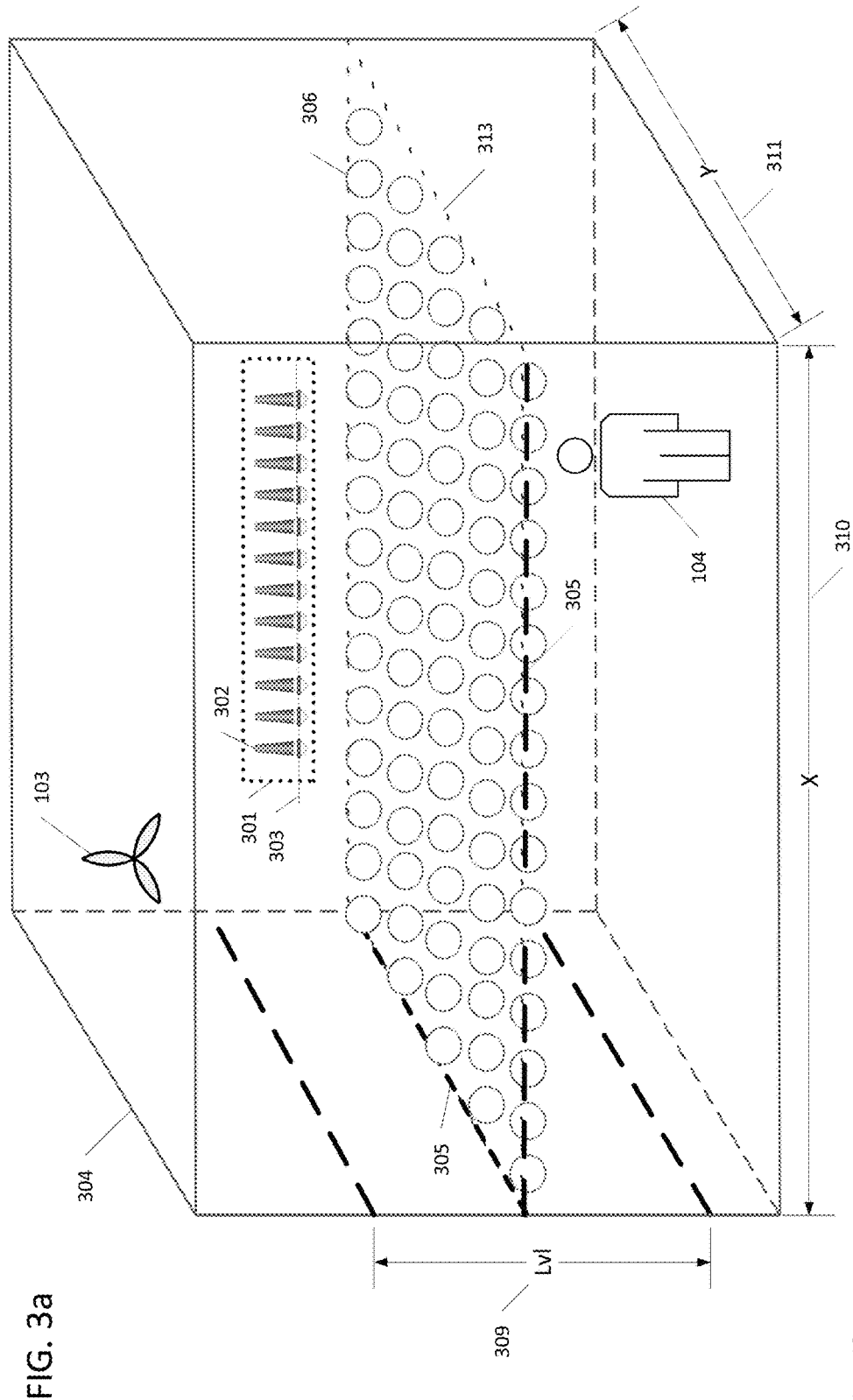
FIGS. 3a and 3b are diagrammatic illustrations of a 2D sound field map and visualization of the sound field reference level with no desired or undesired sound sources.
Figure 3B:
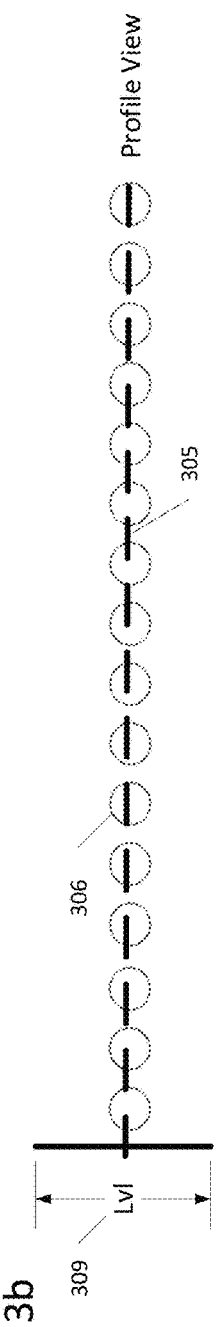
Figure 3C:
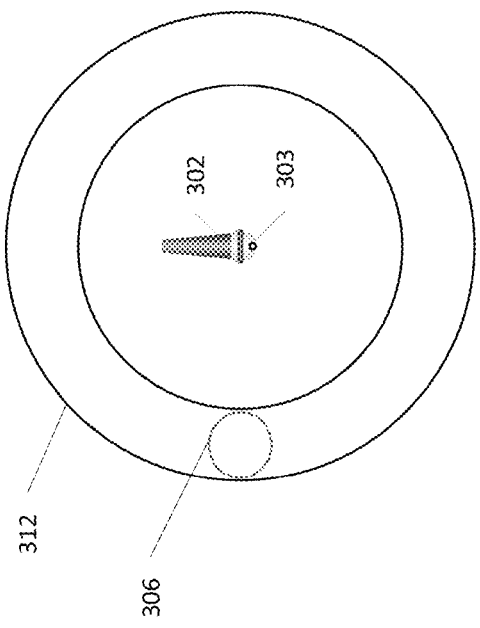
FIG. 3c is a circular coverage pattern diagram.

FIGS. 3a, 3b and 3c disclose a preferred embodiment using a 1D microphone system (array of microphones) 301 to create a plurality of micro-zone(s) 306 in a 2D 310, 311 sound field space 313 while establishing a plurality of intelligent sound field level threshold criteria(s) 309 within each micro-zone 306, to optimize desired sound source 104 pick-up and to minimize undesired sound source 103 pickup by the microphone system 301. It should be noted that micro-zone(s), bubbles, and virtual microphone bubbles can be construed to mean the same thing and be used interchangeably without altering the meaning in the specification.

FIG. 3a illustrates an environment 304 that contains a 1D microphone system 301 that is made up of a plurality of 12 discrete microphones 302. It should be noted that although 12 microphones 302 are shown, the number of microphones 302 contained in the 1D microphone system 301 is a design criterion which could specify more or fewer microphones 302, depending on, but not limited to, the number of micro-zones 306 desired and the amount of space desired to be covered by the microphone system 301. FIGS. 12a and 12b illustrate a non-limiting embodiment of the preferred disclosure that utilizes, but is not limited to, 8192 micro-zones. It should also be noted that for illustrative purposes the micro-zones 306 are shown to be diagrammatically presented against the position coordinate x, 310, y, 311 and z audio sound level (Lvl) 309 axis. The micro-zones 306 are static in position and preferably do not change position in any axis logically or physically. For illustrative purposes, the z axis is labeled Lvl 309 and the micro-zones 306 will be shown with respect to the Lvl 309 axis to demonstrated active (dark grey), target micro-zone (black) to non-active and recalibrated threshold level (white) micro-zone 306 levels. For 2D array installs, FIG. 8 the z coordinate 802 represents a physical height position of the micro-zone 306 such that each micro-zone 306 has a (x, y, z) coordinate value.

Located in the environment 304 is an undesired sound source 103 and a desired sound source 104. For clarity and consistency across the illustrations, the undesired sound source 103 and the desired sound source 104 are shown in static positions; however, the preferred embodiment(s) disclosed is/are able to handle any number of static, dynamic, and moving sound sources 103, 104. In FIG. 3a, neither sound source 103, 104 is emitting sound. The targeting processer 1200 is monitoring all micro-zones 306 simultaneously and has set the intelligent sound field threshold level 305 for each micro-zone 306 based on a specific criterion as outlined in FIG. 12c.

Because there are no active emitting sound sources 103, 104, the threshold levels 309 are uniform across the sound field 313. Since the micro-zones 306 preferably cover a very discrete and defined area in the 2D plane 313, desired 104 and undesired 103 sound sources can preferably be identified, tracked, and isolated based on specific positional, identifiable, and other criteria, thus limiting false positive targeting of undesired sound sources 103 and more reliable positive targeting of desired sound sources 104.

FIG. 3b further illustrates a profile view as seen looking at the micro-zones 306 graphed against the sound field level axis 309. Not all micro-zone(s) 306 are shown and only significant and represented micro-zones 306 are illustrated for clarity.

Figure 8:
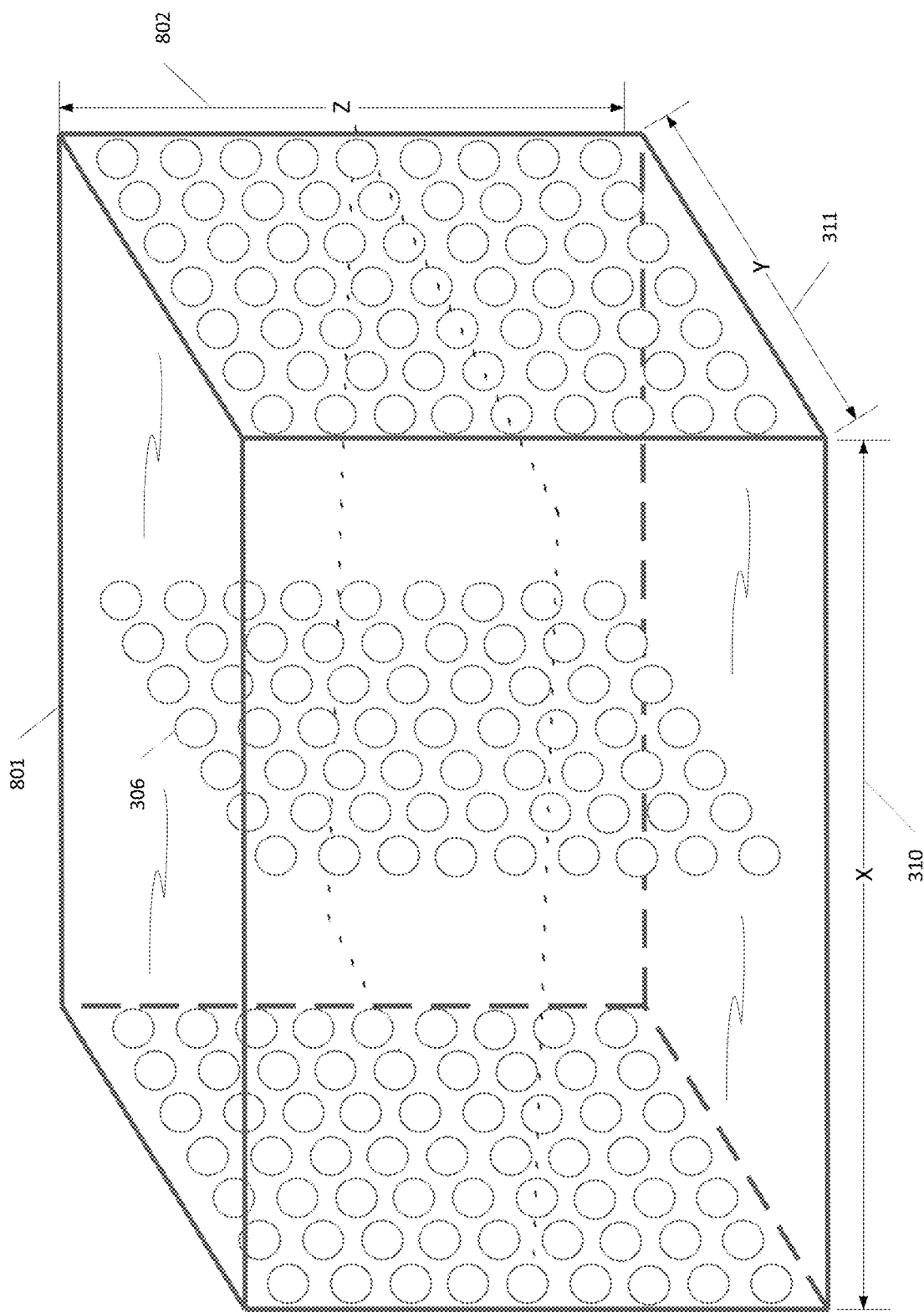
FIG. 8 is diagrammatic illustration of a plurality of micro-zones mapped to a 3D sound field

FIG. 3c illustrated a side view of the 2D micro-zone 306 sound field. A simplification of the system is to constrain all of the microphones 302 into a line 303 in space. Because of the rotational symmetry 312 around the line 303, it is virtually impossible to distinguish the difference between sound sources that originate from different points around a circle 312 that has the line as an axis 303. This turns the microphone micro-zone 306 (bubbles) described above into toroids 312 (essentially rotating the bubble 306 around the microphone axis 303). The micro-zone 306 sample points are constrained to a plane (sound field) 313 extending from one side of the microphone line 303 (one sample point for each toroid). Positions are output from the processor(s) as 2D coordinates with a length and width position coordinate from the microphone array, not as a full 3D coordinate with a height component as illustrated in FIG. 8.

Figure 4A:
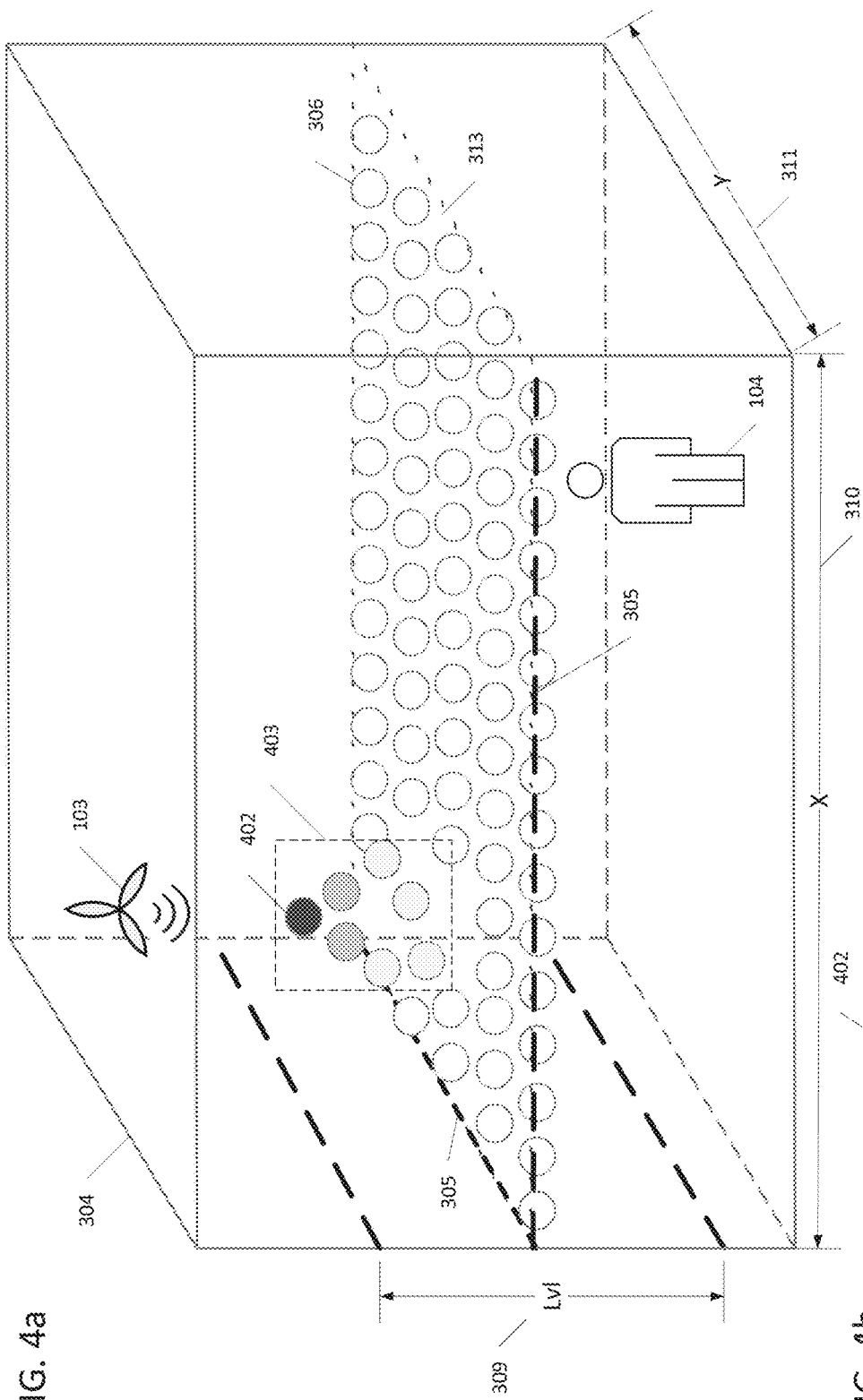
FIGS. 4a and 4b are diagrammatic illustrations of a 2D sound field map and visualization of the sound field reference level with only an undesired sound source.

FIG. 4a illustrates what occurs within the micro-zone(s) 306 sound field 313 when an undesired sound source 103 is emitting sound from a particular position (X,Y) within the environment 304 and the sound field 313. The micro-zone 306 closest (X,Y) to, or receiving the loudest sound source signal (micro-zone 402 in this case) will show the highest Lvl 309 value. Due to the nature of how sound propagates and is picked up, more than one micro-zone 306 will detect the sound source and there will be a plurality of micro-zone(s) 403 that register a Lvl value 309. Typically, the micro-zone with the largest value 402 would be selected by the zone targeting processor 1200 and passed to the audio processing engine 1101. At this point, the intelligent, individual micro-zone(s) 306 sound field threshold level 309 has not been set based on identifying the sound source as an undesired sound source 103. It should be noted that microphone system 301 logically remains in the environment but has been removed from FIGS. 4a, 5a, 6a and 7a for clarity purposes only.

Figure 4B:
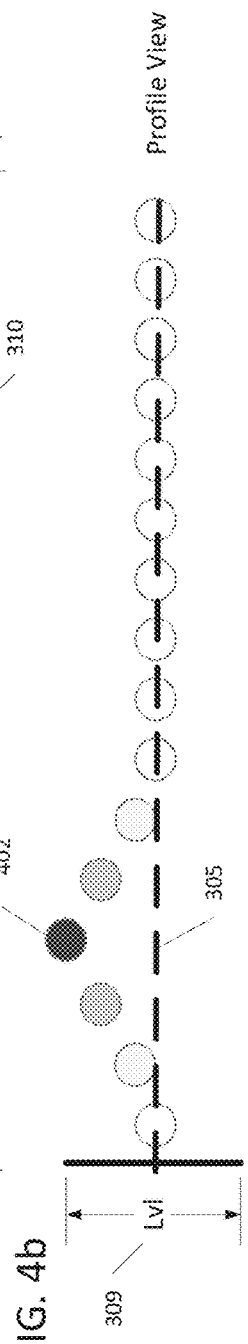

FIG. 4b illustrates what the sound field 313 profile would theoretically look like plotted against the Lvl axis 309, highlighting that micro-zone 402 could potentially be the target micro-zone outputted by the zone target processer 1200.

FIG. 5a further illustrates how the micro-zone 306 sound field 313 is impacted when a desired sound source 104 emits sound concurrently with an undesired sound source 103. The desired sound source 104 will be picked up in the micro-zone(s) 502 that are either closest or have the largest sound source value. In this case, micro-zone 501 registers as the target micro-zone within the group of micro-zone(s) 502. Depending on how the zone targeting processor 1200 logic is implemented, either micro-zone 501 or micro-zone 402 could be selected and passed to the audio processing engine 1101. In the preferred embodiment, the desired sound source 104, micro-zone 501 is selected by the process detailed in FIG. 13 and passed to the audio processing engine 1101. This may not be the case if maximum gain, signal power, and/or other amplitude measurement criteria is used by the targeting engine 1200 as is typical in the current art.

FIG. 5b further illustrates a profile view of the emitting desired sound source 104 and the undesired sound source 103, and the correlation to the micro-zone(s) areas 402, 501. It should be noted that the illustrated levels will often change as the level of the sources change in real-time and will also change the specific micro-zone 306 to directly correspond to the position of the sound sources in relation to the micro-zones as stated previously.

Figures 6A, 6B:
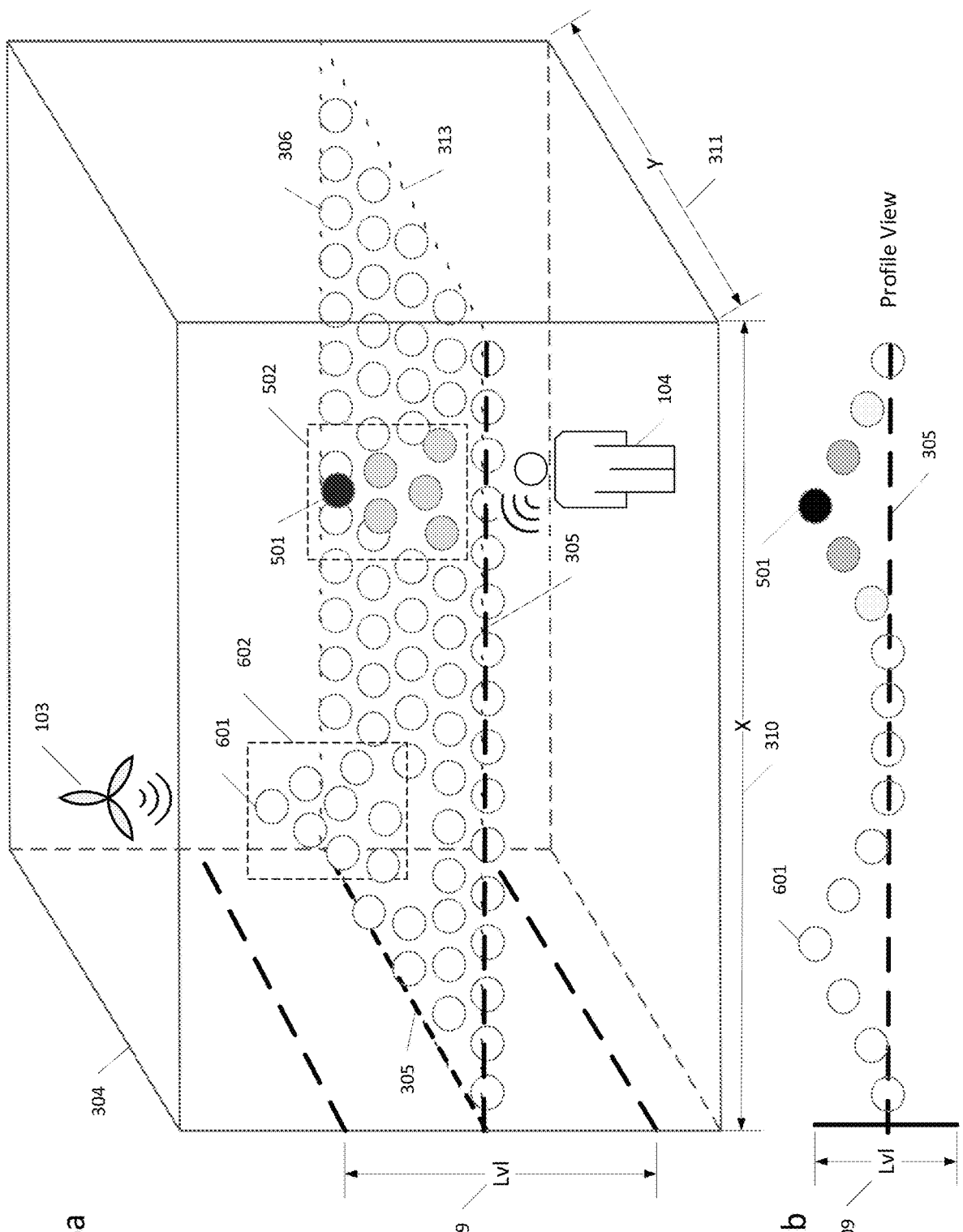
FIGS. 6a and 6b are examples of an embodiment of the present invention applying an intelligent threshold sound field level to a plurality of micro-zones in a 2D sound field.

FIG. 6a discloses a preferred embodiment that will calculate an intelligent micro-zone 306 sound field threshold level 309 based on identifying the sound source in the micro-zone(s) 602 area as undesired. The threshold level 309 typically ranges from, but is not limited to, 20 dB SPL to 80 dB SPL, with a unique value for each micro-zone 306. As an example, assume the background noise level FIG. 3b 305 for a given room is 40 dB. When a persistent or semi-persistent sound source starts FIG. 5a 103, the sound level for that source 402 rises by 10 dB and nearby micro-zones 403 rise by 5 dB leading to detection of a potential target. If the source persists for a long enough period, it is considered part of the background noise and thresholds for the affected micro-zones 402, 403 are adjusted by 10 dB and 5 dB, respectively, to 50 dB and 45 dB, respectively, (FIG. 6a 601, 602) to exclude the undesired source 103. The identification method and threshold calculations will be further explained in FIG. 12c. Because the micro-zone(s) 602 have been identified as undesired sound sources 103, an intelligent threshold sound field level 309 has been set for each micro-zone within 602. The sound field threshold level does two things: First, since an intelligent sound field threshold level has been established, it creates an intelligent sound field threshold level that all sound sources must exceed to be recognized as an active sound source in that micro-zone(s) area 602. The second aspect is that micro-zone(s) 602 have been identified as undesired sound source(s) 103 and will not be recognized as valid, desired sound source targets by the zone targeting processor 1200. This intelligent logic prevents false positive targeting by the zone targeting processor 1200, and only the valid, desired sound source 104, (micro-zone 501) is passed into the audio processing engine 1101 providing optimum audio pick up while minimizing the impact of undesired sound source 103 pick-up. It should be noted that an intelligent threshold sound field level is calculated for each individual micro-zone 306 in near real-time. Active undesired noise source(s) 103 will create the largest offset relative to the reference sound field level 305 while other micro-zones will map to the environmental average sound field level based on their position in the sound field space 313.

FIG. 6b. further illustrates how micro-zone area 602 has become inactive with a higher intelligent threshold sound field level 309, and micro-zone 501 is still active and preferably identified by the zone targeting processor 1200.

Figures 7A, 7B:
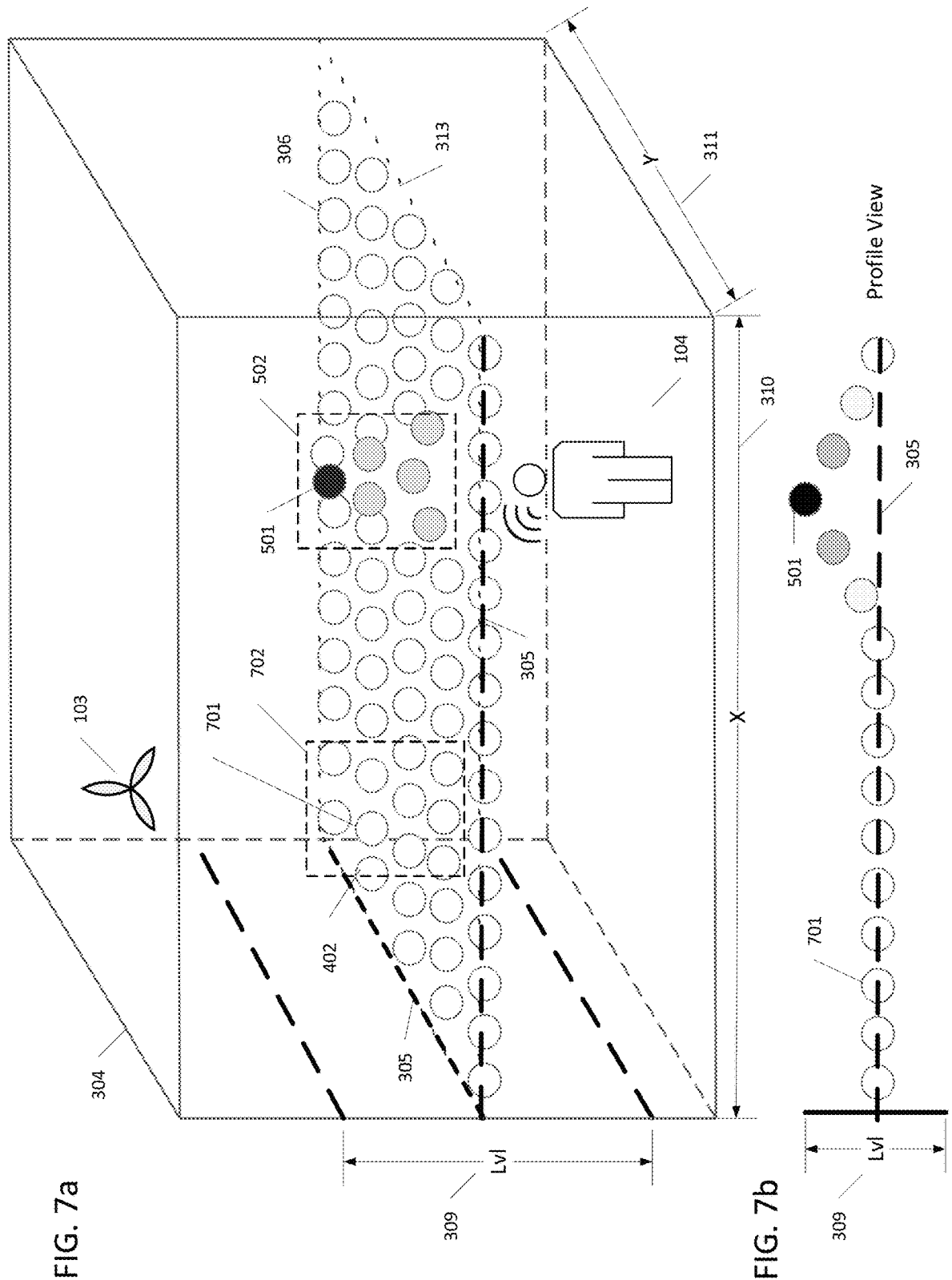
FIGS. 7a and 7b are examples of an embodiment of the present invention adapting the intelligent threshold sound field level to a plurality of micro-zones in a 2D sound field.

FIGS. 7a and 7b illustrate how the micro-zone(s) 306 intelligent threshold sound field level 309 adapts in real-time to dynamic sound source changes. Undesired sound source 103 has stopped emitting sound. The micro-zone(s) area 702 has remapped the individual threshold level(s) 309 to the appropriate environment sound field 313 level 309. Micro-zones 702 have adapted to account for the absence of the undesired sound source 103 and the zone target processor 1200 has recalculated a new intelligent threshold sound field level that takes into account the new sound level 309 at that micro-zone 701 (X,Y) position 310, 311. By responding to dynamic sound source(s), the preferred embodiment is able to adapt, adjust and accommodate for a wide range of undesired sound 103 scenarios without requiring complex configurations, equipment changes, and/or having to accept less than optimal audio performance.

FIG. 8 illustrates an exemplary embodiment of an environment 801 of any dimension that is volumetrically filled with a plurality of micro-zones 306. The zone targeting processor system 1200, as preferred, is set up (but not limited) to measure 8192 concurrent micro-zones (virtual microphone bubbles) 306. The illustration only shows a subset of the micro-zones (virtual microphone bubbles) 306 for clarity. The environment 801 is filled such that from a volumetric perspective all of the volume is preferably covered with the virtual microphone bubbles 306, which are arranged in a 3D grid with (X,Y,Z) vectors 310, 311, 802. By deriving (e.g., calculating) the Process Gain 1208 sourced from each micro-zone location, the exact coordinates of the sound source 103,104 can be measured in an (X,Y,Z) coordinate grid. In addition to Process Gain 1208, an individual intelligent threshold level is derived, as detailed in FIG. 13, for each micro-zone 306. This allows for precise location determination to a high degree of accuracy, which is limited by micro-zone (virtual microphone bubble) 306 size for desired 104 and undesired 103 sound sources. The virtual microphone bubble 306 size and position of each virtual microphone 306 is pre-calculated based on room size and desired bubble size which is configurable to any number of micro-zones. In the preferred embodiment, the number of micro-zones has been defined as 8,192 or 16,384 for typical environment sizes of 30'×30' and 30'×50'. The number of bubbles could range between, but not limited to, 1 to 100,000 micro zones (more preferably, 10 to 50,000 micro zones; more preferably, 20 to 40,000 micro zones; even more preferably, 40 to 30,000 micro zones; more preferably, 60 to 20,000 micro zones; more preferably, 100 to 20,000 micro zones; more preferably, 200 to 10,000 micro-zones), or more, depending on the design criterion. The effective size of the bubbles is a function of the spacing and number of bubbles. For example, in a 10 m by 10 m (100 m$^2$) space with 4 bubbles evenly distributed about the space, effective bubble sizes of approximately 5 m in diameter may be determined. If, preferably, more bubbles are distributed evenly about the 100 m$^2$ space such as 10,000 bubbles the effective bubble size will be approximately 100 cm in diameter. Of course, the bubble sizes may vary depending on the size of the space, the number of wanted and unwanted sound sources, the processing power of the processor(s), etc. It should be noted that the center point of the bubble/micro-zone is used as the reference point for all audio sound source pickup. The microphone level measured is directly related to the quantitative measurement method used such as dB, dBm, sound pressure level (SPL), watts, and/or volts, which is determined by the design criterion and the hardware implementation. The desired embodiment determines a relative threshold regardless of measurement methodology. The virtual microphone bubble parameters include, but are not limited to, size and coordinate position. The parameters are utilized by the zone targeting processor system 1200 throughout the calculation process to derive, including an intelligent threshold sound field level, magnitude and positional information for each of 8,192 or 16,384 virtual microphone bubble 306 position depending on room size. (e.g., [Bubble 1, 0 dB, 1x, 1y], [Bubble 2, 1.1 dB, 1x, 2y] . . . [Bubble 8000, 5 dB, 40x, 200y)]).

A 3D micro-zone sound field 801 is preferably able to discriminate desired 104 and undesired 103 sound sources that are located close together, in the same vector line to the microphone system 301, at the same and or different heights. Since each micro-zone 306 can preferably have a unique intelligent threshold sound level, the microphone system 302 is able to optimize desired sound source 104 pickup while minimizing undesired sound source 103 pickup. Because the microphone system 301 is adapting the micro-zone intelligent threshold sound field level in real-time, the disclosed embodiment is able to overcome the deficiencies in the current art.

FIGS. 9a and 9b illustrate how the targeting processor 1200 can be adapted to address deficiencies in the current art by identifying an undesired sound source 103 and applying an adaptive threshold sound level to that zone to prevent false positive targeting in a typical beam former application.

FIG. 9a illustrates an undesired sound source 103 in Zone 3 and a desired sound source 104 in Zone 5. Zone 1, Zone 2 and Zone 4 are mapped to an ambient sound field threshold level as there are no sound sources present. Zone 3 has an undesired sound source 103 identified by the zone target processor 1200. The zone target processor sets an intelligent threshold sound field level that is at the level of the undesired sound source 103. Within Zone 3, sound sources would have to meet or exceed the intelligent threshold sound field level to become an active target and passed to the audio processing engine 1101. As an hypothetical example, if Zone 3 had an undesired source measured at 10 dB, it would take someone speaking louder than 10 dB in Zone 3 to be considered an active, desired target. However, since Zone 5 contains an active sound source determined to be a desired sound source 104, the array can be steered to the appropriate target without triggering on the undesired sound source 103 in Zone 3 at levels lower than 10 dB.

FIG. 9b further illustrates that two zones can be active in the presence of an undesired sound source. Zone 2 will become the target Zone if the desired sound source 901 is active, since the undesired sound source 103 has been removed as a desired target by the zone target processor. Zone 5 can become active again if the desired sound source 104 exceeds the sound field threshold level for Zone 5. At this point, the desired sound source 104 is competing with the undesired sound source 103, however, this is a limitation of having large zones typical of this type of microphone array topology which does not implement micro-zones 306 which would provide the necessary isolation to better target the desired sound source 104 in a similar situation. As a further example in contrast to FIG. 9a, if the undesired sound source in Zone 5 has a sound level of 10 dB, the desired sound target also in Zone 5 has to be speaking at a level higher than 10 dB to be detected and targeted over the undesired source.

FIG. 10 illustrates adapting the targeting processer 1200 to a discrete microphone setup. In this embodiment, the environment 1002 is set up with four zones (Zone 1, Zone 2, Zone 3 and Zone 4). An undesired sound source 103 straddles Zone(s) 1 and 2. A desired sound source 104 is located in Zone 4. Omni-directional microphones 1001a, 1001b, 1001c, and 1001d are individually located in each Zone as shown. Since the undesired sound source 103 straddles Zone(s) 1 and 2, each zone respectively will have an adaptive reference threshold level set to remove the undesired sound source 103 from the target processer 1200 available targets. This results in microphone 1001d being able to focus on the desired sound source 104 without interference from the undesired sound source 103. If the undesired sound source 103 changes level or turns off completely, then Zone(s) 1 and 2 will remap to the new reference threshold level present at the microphones 1001a, 1001c at that time. It should be noted that the addition of more discrete microphones may preferably shrink the individual zone size which will result in better zone coverage and reduce the likelihood that broad areas of coverage will miss detecting a desired sound source 104 signal.

FIG. 11 demonstrates, at a high level, the two separate processes working within the current embodiment of the system. The system utilizes input from the microphone array 301 which is provided to both the Zone Targeting Processor 1200 and the Audio Processing Engine 1101 via multiple parallel data paths 1105. The Zone Targeting Processor 1200 utilizes the microphone signals 1105 or manually configured information 1106 to determine which source to target and passes that information to the Audio Processing Engine 1101. Using this information, the Audio Processing Engine 1101 optimizes signal processing to provide an optimally processed audio stream 1103. Typically for systems in the current art, microphone inputs 1105 may be optional and instead rely on manual input 1106 using specialized tools and knowledge to configure the shape and size of beams or zones as input to the Zone Targeting Processor 1200. The Zone Targeting Processor 1200 determines which micro-zones contain a sound source and communicates the zone information to the Audio Processing Engine 1101 over a communication interface 1102 which contains zone information, optionally desired and undesired sound levels, and other information as required to optimize audio processing based on knowledge of the desired sound source zone. Communication interface 1102 may be implemented using industry standard or proprietary protocols to provide signals multiplexed over a single physical connection or, optionally, over multiple, separate physical connections. Current art devices are not able to distinguish between desired 104 or undesired sound sources 103 and thus can erroneously target undesired sources 103 of persistent or semi-persistent sound such as projector fans, HVAC (Heating, Ventilation, Air Conditioning) fans/vents, room display fans or any other electronic or mechanical devices; this limitation is especially apparent is current art devices where beams or zones are manually configured, and typically cover broad areas within the environment.

The preferred embodiment(s) of the invention is/are implemented in the Zone Targeting Processor 1200 and only influence(s) how the Audio Processing Engine 1101 performs its processing by utilizing knowledge of zones containing desired 104 or undesired 103 sound sources. The Audio Processing Engine 1101 performs primary echo cancellation, secondary echo and noise reduction, and any other processing as may be implemented by current art devices on the microphone signals prior to outputting the fully processed audio signal 1103. The disclosed methods and apparatus is/are used to exclude undesired sound sources 103 from consideration as a targeted source, thereby reducing the likelihood that desired sound sources 104 are either (i) missed partially during a transition from an undesired 103 to a desired source 104 or (ii) missed completely due to the undesired sound source 103 overpowering the desired sound source 104. The targeting mechanism embodied by the invention can be applied to any audio system comprising multiple microphones used to monitor and capture audio signals in multiple zones including, but not limited to, beamforming microphone arrays and discrete microphone systems FIGS. 2a-2g.

FIGS. 12a, 12b, and 12c are functional diagrams of the Zone Targeting (bubble) Processor, and also illustrated is a flow chart FIG. 13 outlining the logic to derive the processing gain to identify the position of the desired sound source 1209. A purpose of the system is to create an improved sound output signal 1215 by combining the inputs from the individual microphone elements 302 in the array 301 in a way that increases the magnitude (e.g., amplitude) of the direct sound 1401 received at the microphone array relative to the reverb 1402 and noise 1403 components. For example, if the magnitude of the direct signal 1401 can be doubled relative to the others signals 1402, 1403, it will have roughly the same effect as halving the distance between the microphones 302 and the sound source 1209. The signal strength when the array is focused on a sound source 1209 divided by the signal strength when the array is not focused on any sound source 1209 (such as ambient background noise, for example) is defined as the processing gain of the system. The preferred embodiment(s) work by setting up thousands of listening positions (as shown in FIG. 8 and explained below) within the room, and simultaneously measuring the processing gain at each of these locations. The virtual listening position with the largest processing gain is preferably the location of the sound source 1209.

To derive the processing gains 1208, the volume of the room where sound pickup is desired is preferably divided into a large number of virtual microphone positions (FIG. 8). When the array is focused on a given virtual microphone 306, then any sound source within a close proximity of that location will produce an increased processing gain sourced from that virtual microphone 306. The volume around each virtual microphone 306 in which a sound source will produce maximum processing gain at that point, is defined as a bubble. Based on the location of each microphone and the defined 3D location for each virtual microphone and using the speed of sound, which can be calculated given the current measured room temperature, the system 1200 can determine the expected propagation delay from each virtual microphone 306 to each microphone array element 302.

The flow chart in FIG. 12a illustrates the signal flow within the bubble processing unit 1200. This example preferably monitors 8192 bubbles simultaneously. The sound from each microphone element 302 is sampled at the same time as the other elements within the microphone array 301 and at a fixed rate of 12 kHz or higher depending on processing capability. Each sample is passed to a microphone element processor 1201 illustrated in FIG. 12b. The microphone element processor 1201 preferably conditions and aligns the signals in time and weights the amplitude of each sample so they can be passed on to the summing node 1204.

The signal components (1220) from the microphone's element processor 1201 are summed at node 1204 to provide the combined microphone array 301 signal for each of the 8192 bubbles. Each bubble signal is preferably converted into a power signal at node 1205 by squaring the signal samples. The power signals are then preferably summed over a given time window ranging from 1 ms to 10 seconds, (more preferably, 10 ms to 5 seconds; even more preferably, 20 ms to 3 seconds, more preferably, 50 ms to 1 second, most preferably about 100 ms) by the 8192 accumulators at node 1207. The sums represent the signal energy over that time period.

The processing gain for each bubble is preferably calculated at node 1208 by dividing the energy of each bubble by the energy of an ideal unfocused signal 1222. The unfocused signal energy is preferably calculated by Summing 1219 the energies of the signals from each microphone element 1218 over the given time window (e.g., 1 ms to 10 seconds, preferably 100 ms), weighted by the maximum ratio combining weight squared. This is the energy that is expected if all of the signals were uncorrelated. The processing gain 1208 is then preferably calculated for each bubble by dividing the microphone array signal energy by the unfocused signal energy 1222.

Processing Gain is achieved because signals from a common sound source all experience the same delay before being combined, which results in those signals being added coherently, meaning that their amplitudes add up. If twelve equal amplitude and time aligned direct signals 1401 are combined, the resulting signal will have an amplitude 12×  higher, or a power level 144× higher. Signals from different sources and signals from the same source with significantly different delays as the signals from reverb 1402 and noise 1403 do not add up coherently and do not experience the same gain. In the twelve extremes, the signals are completely uncorrelated and will add up orthogonally. If twelve equal amplitude orthogonal signals are added, the signal will have roughly 12× the power of the original signal or a 3.4× increase in amplitude (measured as rms). The difference between the 12× gain of the direct signal 1401 and the 3.4× gain of the reverb (1402) and noise signals (1403) is the net processing gain (3.4× or 11 dB) of the microphone array 301 when it is focused on the sound source 1209. This makes the signal sound as if the microphone 302 has moved 3.4× closer to the sound source. The example used is a twelve microphone array 301, but it could be extended to an arbitrary number (N) resulting in a maximum possible processing gain of sqrt(N) or 10 log (N) dB.

The bubble processor system 1200 preferably simultaneously focuses the microphone array 301 on 8192 points 306 in 3-D space using the method described above. The energy level of a short burst of sound signal (50-100 ms) is measured at each of the 8192 virtual microphone bubble 306 points and compared to the energy level that would be expected if the signals combined orthogonally. This gives the processing gain 1208 at each point. The virtual microphone bubble 306 that is closest to the sound source 1209 should experience the highest processing gain and be represented as a peak in the output. Once that is determined, the location 310 is known.

FIG. 12*c* expands upon the reference sound field adjustment module 1202 in FIG. 12*a*. The goal is to use the bubble processor to locate an active signal source and focus on it in the presence of undesired sound source 103. The microphone element 1218 passes down microphone signals 1203 which are used by the ambient noise detector 12022 to determine when the room is in a state of ambient noise, meaning no desired sound is present. The current implementation involves calculating the mean microphone power over $t_1$ seconds (for example, a minimum of 10 milliseconds, maximum of 10 seconds, preferably about 0.5 seconds). Then, the lowest microphone power over $t_2$ seconds (where $t_2$ is a multiple of $t_1$, preferably 20 seconds, preferred minimum 5 seconds, preferred maximum 10 minutes) is saved as an estimate of the power of the reference sound field. This is repeated over the course of $t_3$ seconds (where $t_3$ is a multiple of $t_2$, preferably 200 seconds, preferred minimum 20 seconds, preferred maximum 60 minutes) and the reference sound field power estimates that are collected are simply averaged to get a more accurate result. Outliers are removed before averaging, preferably by ignoring a few of the largest reference sound field power estimates that could be a result of constant speech over $t_2$ seconds. The current microphone power is compared to the reference sound field power against a tunable threshold value, which typically ranges from 5 dB to 10 dB. The threshold value is preferably tuned according to statistical analysis on a variety of room conditions, to find the optimal threshold with the lowest amount of false detections while maintaining a high success rate. For example, a relatively quiet room may have a threshold of 5 dB while a larger, noisier room might have a threshold of 8 or 10 dB. Comparing the current microphone power to the reference sound field power determines whether or not the room is in a reference state, or if there is an active signal. When the room is confirmed to be in a reference state, the 8192 bubble/micro-zone array 12021, which is obtained from the processing gain unit 1208 is saved repeatedly (may be in real-time) and averaged through the bubble/micro zone reference array generator 12023 resulting in a bubble/micro zone array that represents only the background sound field in the room. This bubble/micro zone reference array 12024 is stored (1216) and subtracted from the current bubble/micro zone array 12021 through the reference-subtracted bubble/micro zone array generator 12025 to create a resulting bubble/micro zone array that only contains the desired sound field (12026). By using this resulting array 12026, the desired signal source position can be obtained in the presence of loud ambient noise sources through the source signal position identifying module 1206. The 8192 1D output reference subtracted bubble/micro zone array is stored (1215) for any additional processing.

Node 1206 preferably searches through the output of the reference sound field adjustment unit 1202 for the bubble/micro zone with the highest processing gain. The (X, Y, Z) location 310, 311, 802, of the virtual microphone 306 corresponding to that bubble can then be determined by looking up the index in the original configuration to determine the exact location of the Sound Source 1209. The parameters 1214 may be communicated to various electronic devices to focus them to the identified sound source position 310. After deriving the location 310 of the sound source 1209, focusing the microphone array 301 on that sound source 1209 is accomplished after achieving the gain. The Bubble processor 1200 is designed to find the sound source 1209 quickly enough so that the microphone array 301 can be focused while the sound source 1209 is active (and may be moving) which can be a very short window of opportunity. The bubble processor system 1200 according to this embodiment is able to find new sound sources in less than 100 ms. Once found, the microphone array focuses on that location to pick up the sound source signal 1210 and the system 1200 reports the location of the sound through the Identify Source Signal Position 1206 to other internal processes such as microphone array control for delay, gain processing and stereo microphone processing (such as stereo signal generation, binaural audio and or other audio perceptive processing processes) and to the host computer, so that it can implement sound sourced location-based applications such as real-time tracking of desired source targets and display of persistent or semi-persistent undesired sound sources. Preferably, this is a function of the bubble processor 1200.

The Mic Element Processor 1201 as shown in FIG. 12*b*, is preferably the first process used to focus the microphone array 301 on a particular bubble 306. Individual signals from each microphone 302 are preferably passed to a Precondition process 12017 (FIG. 12*b*). The Precondition process 12017 filters off low frequency and high frequency components of the signal resulting in an operating bandwidth of 200 Hz to 1000 Hz.

A delay line 12011 (FIG. 12*a*) preferably stores the pre-conditioned sample plus a finite number of previously pre-conditioned samples from that microphone element 302. During initialization, the fixed virtual microphone 306 positions and the calculated microphone element 302 positions are known. For each microphone element 302, the system preferably calculates the distance to each virtual microphone 306 then computes the added delay needed for each virtual microphone and preferably writes it to delay look up table 12012. It also computes the maximal ratio, combining weight for each virtual microphone 306, and stores that in the weight lookup table 12014.

A counter 12015, preferably running at a sample frequency of more than 8192 times that of the microphone sample rate, counts bubble positions from 0 to 8191 and sends this to the index of the two look up tables 12012 and 12014. The delay due to distance from the bubble to microphone is determined 12016 and used with the bubble position to look up the bubble specific weighting to use 12014. The output of the bubble delay lookup table 12012 is preferably used to choose that tap of the delay line 12011 with the corresponding delay for that bubble. That sample is then preferably multiplied 12013 by the weight read from the weight lookup table 12014. For each sample input to the microphone element processor 1201, 8192 samples are output 12018, each corresponding to the signal component for a particular virtual microphone bubble 306 in relation to that microphone element 302.

FIG. 13 depicts the logical flow of the reference sound field adjustment module 1202 in FIG. 12a. The steps are described below:

S1001—Start the process of removing the reference sound field from active sound field to obtain only desired signals for targeting.

S1002—Accumulate microphone power $P_M$ over $t_1$ seconds and average. The number of samples $N_1$ is determined by time $t_1$ and sample rate.

S1003—Repeat step S1002 for $t_2$ seconds and save the lowest microphone power. This is an estimate of the reference sound power.

S1004—Repeat step S1003 for $t_3$ seconds to accumulate estimated reference power levels $P_R$. Time $t_3$ is determined by the reference sound power sample size $N_2$ multiplied by $t_2$. Average to obtain the final estimate of the reference power $P_{RA}$. Outliers with $P_R$>A where A is a tunable threshold should be removed from the averaging.

S1005—The current average microphone power $P_{MA}$ over $t_1$ seconds is compared to $P_{RA}$ against a configurable threshold. If $P_{MA}$<$P_{RA}$ B, where B is a configurable threshold, then save the current 8 k bubble/micro zone array as the reference sound field $P_R$.

S1006—Compute the average reference sound field $P_{BA}(x)$ to achieve a better estimate. The greater the number of arrays $N_3$, the more accurate the reference sound field estimate will be.

S1007—Subtract the reference sound field $P_{BA}(x)$ from the current 8 k bubble/micro zone array $P_{BC}(x)$ to obtain the reference subtracted bubble/micro zone array $P_N(x)$.

S1008—With the final reference subtracted bubble/micro zone array, it is now possible to apply signal targeting with greater accuracy to desired sound by having removed the undesired sound field.

S1009—The process of removing the reference sound field from the active sound field is complete.

Figure 14B:
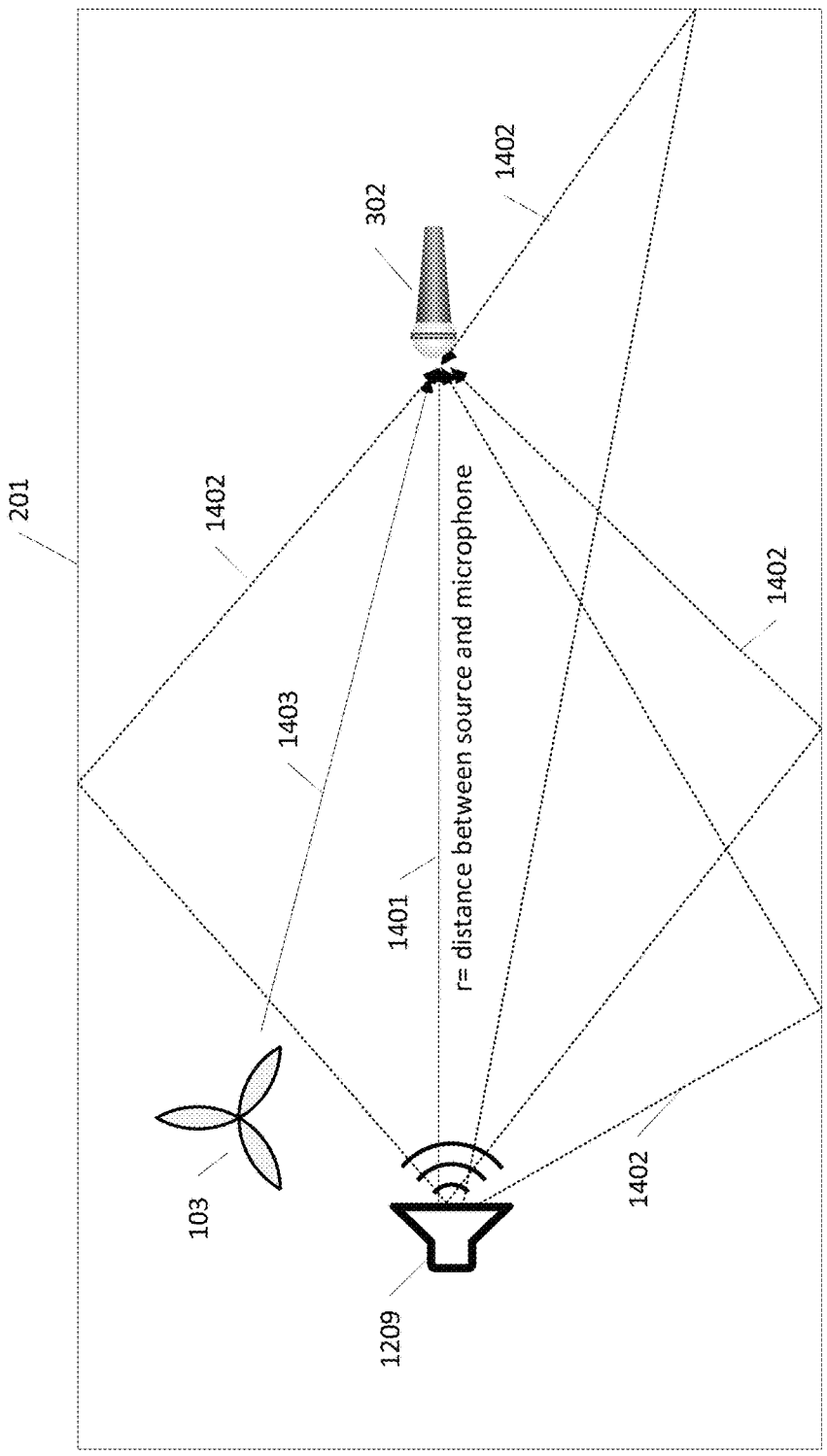

FIGS. 14a and 14b illustrate that as microphone 302 is physically separated through distance from the sound source 1209, the direct path's 1401 sound pressure 1403 level drops predictably following the l/r rule 1404, however the accumulation of the reflected paths 1402 tend to fill the environment 201 more evenly. As one moves the microphone 302 further from the sound source 1209, the reflected sound waves 1402 make up more of the microphone 302 measured signal. The measured signal sounds much more distant and harder to hear, even if it has sufficient amplitude, as the reflected sound waves 1402 are dispersed in time, which causes the signal to be distorted, and effectively not as clear to a listener.

The embodiments described in this application have been presented with respect to use in one or more conference rooms preferably with local and multiple remote users. However, the present invention may also find applicability in other environments such as: 1. Commercial transit passenger and crew cabins such as, but not limited to, aircraft, busses, trains and boats. All of these commercial applications can be outfitted with microphones and speakers which can benefit from consistent microphone audio signal quality with minimal echo signal conditions which can vary from moderate to considerable; 2. Private transportation such as cars, truck, and mini vans, where command and control applications and voice communication applications are becoming more prominent; 3. Industrial applications such as manufacturing floors, warehouses, hospitals, and retail outlets to allow for audio monitoring and to facilitate employee communications without having to use specific portable devices; and 4. Drive through windows and similar applications, where ambient sounds levels can be quite high and variable, can be controlled to consistent levels within the scope of the invention. Also, the processing described above may be carried out in one or more devices, one or more servers, cloud servers, etc.

The individual components shown in outline or designated by blocks in the attached Drawings are all well-known in the electronic processing arts, and their specific construction and operation are not critical to the operation or best mode for carrying out the invention.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An apparatus targeting one or more undesired sound source(s) in a space having a plurality of microphones and at least one desired sound source, comprising:
at least one microphone input that receives plural microphone input signals from the plurality of microphones in the space;
at least one processor, coupled to said at least one microphone input and receiving the plural microphone input signals;
the at least one processor determining plural virtual microphone bubbles in the space;
the at least one processor determining a threshold sound field level, utilizing processing in a time domain, for each virtual microphone bubble based on the received plural microphone input signals that correspond to (i) virtual microphone bubbles located within ambient background noise and (ii) virtual microphone bubbles located at the one or more undesired sound source(s) in the space; and
the at least one processor recognizing a desired sound source when the received plural microphone input signals exceed one or more threshold sound field levels.

2. The apparatus according to claim 1, wherein the at least one processor determines a threshold sound field level for each virtual microphone simultaneously.

3. The apparatus according to claim 2, wherein the at least one processor determines the plural virtual microphone bubbles in the space continuously.

4. The apparatus according to claim 1, wherein the at least one processor mitigates at least one undesired sound source(s) prior to audio processing of noise suppression.

5. The apparatus according to claim 1, wherein the at least one processor determines the plural virtual microphone bubbles as a 2D array.

6. The apparatus according to claim 1, wherein the at least one processor determines the plural virtual microphone bubbles as a 3D array.

7. The apparatus according to claim 1, wherein the at least one processor recognizes a desired sound source which is moving through plural virtual microphone bubbles in the space.

8. The apparatus according to claim 1, wherein the at least one processor mitigates at least one undesired sound source that is moving through plural virtual microphone bubbles in the space.

9. The apparatus according to claim 1, wherein the at least one processor comprises at least one zone target processor and at least one audio processing engine.

10. The apparatus according to claim 1, wherein the at least one processor calculates processing gain of the received plural microphone input signals in the space after determining plural virtual microphone bubbles in the space.

11. The apparatus according to claim 1, wherein the at least one processor provides at least one target signal to target the plurality of microphones on the recognized desired sound source.

12. The apparatus according to claim 1, wherein the at least one processor determining a threshold sound field level based on a manual input.

13. A method of targeting one or more undesired sound source(s) in a space having a plurality of microphones and at least one desired sound source, comprising:
using at least one microphone input to receive plural microphone input signals from the plurality of microphones in the space; and
using at least one processor, coupled to said at least one microphone input and receiving the plural microphone input signals, to:
determine plural virtual microphone bubbles in the space;
determine a threshold sound field level, utilizing processing in a time domain, for each virtual microphone bubble based on the received plural microphone input signals that that correspond to (i) virtual microphone bubbles located within ambient background noise and (ii) virtual microphone bubbles located at the one or more undesired sound source(s) in the space; and
recognize a desired sound source when the received plural microphone input signals exceed one or more threshold sound field levels.

14. The method according to claim 13, wherein the at least one processor determines a threshold sound field level for each virtual microphone bubble simultaneously.

15. The method according to claim 14, wherein the at least one processor determines the plural virtual microphone bubbles in the space continuously.

16. The method according to claim 13, wherein the at least one processor wherein the at least one processor mitigates at least one undesired sound source(s) prior to audio processing of noise suppression.

17. The method according to claim 13, wherein the at least one processor determines the plural virtual microphone bubbles as a 2D array.

18. The method according to claim 13, wherein the at least one processor determines the plural virtual microphone bubbles as a 3D array.

19. The method according to claim 13, wherein the at least one processor recognizes a desired sound source which is moving through plural virtual microphone bubbles in the space.

20. The method according to claim 13, wherein the at least one processor mitigates at least one undesired sound source that is moving through plural virtual microphone bubbles in the space.

21. The method according to claim 13, wherein the at least one processor comprises at least one zone target processor and at least one audio processing engine.

22. The method according to claim 13, wherein the at least one processor calculates processing gain of the received plural microphone input signals in the space after determining plural virtual microphone bubbles in the space.

23. An apparatus mitigating one or more undesired sound source(s) in a space having at least one microphone and at least one desired sound source, comprising:
at least one microphone input that receives microphone input signals from the at least one microphone in the space;
at least one processor, coupled to said at least one microphone input and receiving the microphone input signals;
the at least one processor determining plural virtual microphone bubbles in the space;
the at least one processor determining a threshold sound field level, utilizing processing in a time domain, for each virtual microphone bubble based on the received microphone input signals that correspond to the one or more undesired sound source(s) in the space; and
the at least one processor recognizing a desired sound source when the received microphone input signals exceed one or more threshold sound field levels.

24. At least one non-transitory computer readable media for mitigating one or more undesired sound source(s) in a space having at least one microphone and at least one desired sound source, said non-transitory computer readable media comprising instructions causing at least one processor to:
use at least one microphone input to receive plural microphone input signals from the plurality of microphones in the space;
use at least one processor, coupled to said at least one microphone input and receiving the plural microphone input signals, to:
determine plural virtual microphone bubbles in the space;
determine a threshold sound field level, utilizing processing in a time domain, for each virtual microphone bubble based on the received plural microphone input signals that correspond to the one or more undesired sound source(s) in the space; and
recognize a desired sound source when the received plural microphone input signals exceed one or more threshold sound field levels.

* * * * *